United States Patent [19]
McLaughlin-Taylor et al.

[11] Patent Number: 6,114,113
[45] Date of Patent: Sep. 5, 2000

[54] HIGH EFFICIENCY GENETIC MODIFICATION METHOD

[75] Inventors: Elizabeth McLaughlin-Taylor, San Clemente; Mark Kruger, Encinitas; Cheryl Lundak, San Diego; Catherine Killion, Long Beach, all of Calif.

[73] Assignee: Chiron Corporation, Emeryville, Calif.

[21] Appl. No.: 09/132,541

[22] Filed: Aug. 11, 1998

Related U.S. Application Data

[60] Provisional application No. 60/055,453, Aug. 11, 1997.

[51] Int. Cl.[7] .............................. C12Q 1/68; C12Q 1/70; C12N 15/86
[52] U.S. Cl. .............................. 435/5; 435/440; 435/455; 435/456; 435/372.3
[58] Field of Search .......................... 514/44; 435/320.1, 435/235.1, 325, 375, 440, 455; 424/93.1, 93.2

[56] References Cited

FOREIGN PATENT DOCUMENTS

| | | |
|---|---|---|
| WO 94/29436 | 12/1994 | WIPO . |
| WO 95/14091 | 5/1995 | WIPO . |
| WO 95/33823 | 12/1995 | WIPO . |
| WO 96/21014 | 7/1996 | WIPO . |
| WO 96/25433 | 8/1996 | WIPO . |
| WO 96/33282 | 10/1996 | WIPO . |

OTHER PUBLICATIONS

Anderson. Human Gene Therapy. Nature. vol. 392. Supp. pp. 25–30, Apr. 30, 1998.

Verma et al. Gene Therapy—Promises, Problems and Prospects. Nature. vol. 389. pp. 239–242, Sep. 18, 1997.

Orkin et al. Report and Recommendations of the Panel to Assess the NIH Investment in Research on Gene Therapy, Dec. 7, 1995.

AH–1 Rudoll et al., "High–Efficiency Retroviral Vector Mediated Gene Transfer into Human Peripheral Blood $CD4^+$," *Gene Therapy* 3:695–705 (1996).

*Primary Examiner*—David Guzo
*Assistant Examiner*—Jon Shuman
*Attorney, Agent, or Firm*—Robins and Associates; Robert P. Blackburn

[57] ABSTRACT

A method is provided for producing a population of genetically modified T cells. In the method, an in vitro population of T cells is activated by contacting said population with a CD3 binding agent. Genetic modification is then carried out with the activated T cells by contacting the same with a suitable gene transfer vector.

50 Claims, 3 Drawing Sheets

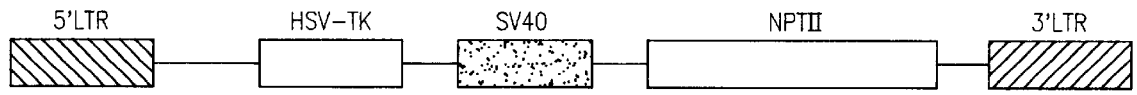
FIG. 3
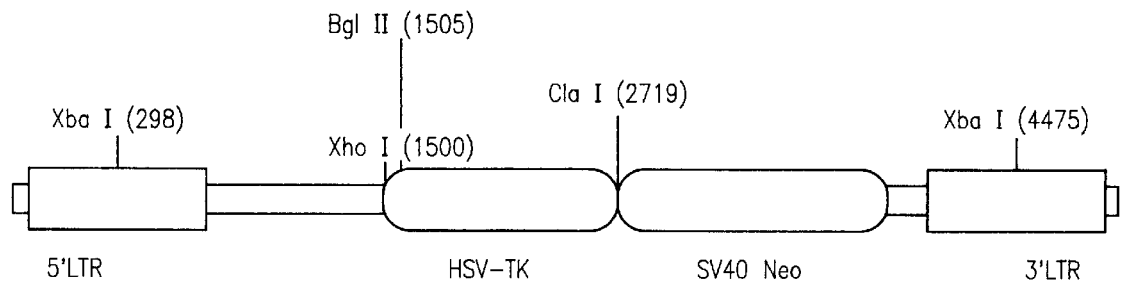
FIG. 4A
| Bases | Functional Description |
|---|---|
| 1-593 | MoMLV 5'LTR |
| 594-1499 | MoMLV Packaging Signal |
| 1500-2719 | HSV-TK |
| 2720-3184 | SV40 Early Promoter and Origin |
| 3185-4035 | neo$^r$ Gene |
| 4036-4175 | MoMLV 3' Noncoding Region and Polypurine Tract |
| 4176-4768 | MoMLV 3'LTR |
| 4769-7453 | pUC19 Plasmid Backbone |
FIG. 4B

SEQUENCE LISTING

<160> NUMBER OF SEQ ID NOS: 21

<210> SEQ ID NO 1
<211> LENGTH: 32
<212> TYPE: DNA
<213> ORGANISM: Unknown
<220> FEATURE:
<223> OTHER INFORMATION: Description of Unknown Organism:This
      information is not available.

<400> SEQUENCE: 1
gggagtggta acagtctggc cttaattctc ag                              32

<210> SEQ ID NO 2
<211> LENGTH: 23
<212> TYPE: DNA
<213> ORGANISM: Unknown
<220> FEATURE:
<223> OTHER INFORMATION: Description of Unknown Organism:This
      information is not available.

<400> SEQUENCE: 2
cggtcgacct cgagaattaa ttc                                        23

<210> SEQ ID NO 3
<211> LENGTH: 23
<212> TYPE: DNA
<213> ORGANISM: Unknown
<220> FEATURE:
<223> OTHER INFORMATION: Description of Unknown Organism:This
      information is not available.

<400> SEQUENCE: 3
ctgggagacg tcccagggac ttc                                        23

<210> SEQ ID NO 4
<211> LENGTH: 32
<212> TYPE: DNA
<213> ORGANISM: Unknown
<220> FEATURE:
<223> OTHER INFORMATION: Description of Unknown Organism:This
      information is not available.

<400> SEQUENCE: 4
ggccagactg ttaccactcc ctgaagtttg ac                              32

<210> SEQ ID NO 5
<211> LENGTH: 30
<212> TYPE: DNA
<213> ORGANISM: Unknown
<220> FEATURE:
<223> OTHER INFORMATION: Description of Unknown Organism:This
      information is not available.

<400> SEQUENCE: 5
catcgataaa ataaaagatt ttatttagtc                                 30

<210> SEQ ID NO 6
<211> LENGTH: 22
<212> TYPE: DNA
<213> ORGANISM: Unknown
<220> FEATURE:
<223> OTHER INFORMATION: Description of Unknown Organism:This
      information is not available.

<400> SEQUENCE: 6
caaatgaaag accccegctg ac                                              22

<210> SEQ ID NO 7
<211> LENGTH: 51
<212> TYPE: DNA
<213> ORGANISM: Unknown
<220> FEATURE:
<223> OTHER INFORMATION: Description of Unknown Organism:This
      information is not available.

<400> SEQUENCE: 7
tcgaggggcc cagatctgcg gccgctcgcg agtcgacaag cttggatcca t              51

<210> SEQ ID NO 8
<211> LENGTH: 49
<212> TYPE: DNA
<213> ORGANISM: Unknown
<220> FEATURE:
<223> OTHER INFORMATION: Description of Unknown Organism:This
      information is not available.

<400> SEQUENCE: 8
cgatggatcc aagcttgtcg actcgcgagc ggccgcagat ctgggcccc                 49

<210> SEQ ID NO 9
<211> LENGTH: 39
<212> TYPE: DNA
<213> ORGANISM: Unknown
<220> FEATURE:
<223> OTHER INFORMATION: Description of Unknown Organism:This
      information is not available.

<400> SEQUENCE: 9
gaagcttctc ccagaaccca ccagtcttga aacgccatc                            39

<210> SEQ ID NO 10
<211> LENGTH: 25
<212> TYPE: DNA
<213> ORGANISM: Unknown
<220> FEATURE:
<223> OTHER INFORMATION: Description of Unknown Organism:This
      information is not available.

<400> SEQUENCE: 10
gtaccagctt ttggtctcat caaag                                           25

<210> SEQ ID NO 11
<211> LENGTH: 36
<212> TYPE: DNA
<213> ORGANISM: Unknown
<220> FEATURE:
<223> OTHER INFORMATION: Description of Unknown Organism:This
      information is not available.

<400> SEQUENCE: 11
ctcctcgagc taaagatatt ttagagaaga attaac                               36

<210> SEQ ID NO 12
<211> LENGTH: 25
<212> TYPE: DNA
<213> ORGANISM: Unknown
<220> FEATURE:
<223> OTHER INFORMATION: Description of Unknown Organism:This
      information is not available.

<400> SEQUENCE: 12

-continued

```
ttcctctgga cagctgtcta ctttg                                          25

<210> SEQ ID NO 13
<211> LENGTH: 20
<212> TYPE: DNA
<213> ORGANISM: Unknown
<220> FEATURE:
<223> OTHER INFORMATION: Description of Unknown Organism:This
      information is not available.

<400> SEQUENCE: 13
caccgtcgtc gacttatgct                                                20

<210> SEQ ID NO 14
<211> LENGTH: 34
<212> TYPE: DNA
<213> ORGANISM: Unknown
<220> FEATURE:
<223> OTHER INFORMATION: Description of Unknown Organism:This
      information is not available.

<400> SEQUENCE: 14
gaccgtcgac tcaattctgg gagaagcttc ttgg                                34

<210> SEQ ID NO 15
<211> LENGTH: 20
<212> TYPE: DNA
<213> ORGANISM: Unknown
<220> FEATURE:
<223> OTHER INFORMATION: Description of Unknown Organism:This
      information is not available.

<400> SEQUENCE: 15
caccgtcgtc gacttatgct                                                20

<210> SEQ ID NO 16
<211> LENGTH: 30
<212> TYPE: DNA
<213> ORGANISM: Unknown
<220> FEATURE:
<223> OTHER INFORMATION: Description of Unknown Organism:This
      information is not available.

<400> SEQUENCE: 16
caacgctcga gaagcagaat cgcaaaaggc                                     30

<210> SEQ ID NO 17
<211> LENGTH: 32
<212> TYPE: DNA
<213> ORGANISM: Unknown
<220> FEATURE:
<223> OTHER INFORMATION: Description of Unknown Organism:This
      information is not available.

<400> SEQUENCE: 17
tcggctcgag gcatcaacgg gaaataactc gt                                  32

<210> SEQ ID NO 18
<211> LENGTH: 31
<212> TYPE: DNA
<213> ORGANISM: Unknown
<220> FEATURE:
<223> OTHER INFORMATION: Description of Unknown Organism:This
      information is not available.

<400> SEQUENCE: 18
ccgactcgag tcagtagagg tcctgtgcct c                                   31
```

```
<210> SEQ ID NO 19
<211> LENGTH: 26
<212> TYPE: DNA
<213> ORGANISM: Unknown
<220> FEATURE:
<223> OTHER INFORMATION: Description of Unknown Organism:This
      information is not available.

<400> SEQUENCE: 19
gcgactcgag catggggccc tggggc                                    26

<210> SEQ ID NO 20
<211> LENGTH: 21
<212> TYPE: DNA
<213> ORGANISM: Unknown
<220> FEATURE:
<223> OTHER INFORMATION: Description of Unknown Organism:This
      information is not available.

<400> SEQUENCE: 20
gcactggaat tcgtcagggc g                                         21

<210> SEQ ID NO 21
<211> LENGTH: 16
<212> TYPE: DNA
<213> ORGANISM: Unknown
<220> FEATURE:
<223> OTHER INFORMATION: Description of Unknown Organism:This
      information is not available.

<400> SEQUENCE: 21
tgcatgcctg caggtc                                               16
```

HIGH EFFICIENCY GENETIC MODIFICATION METHOD

CROSS-REFERENCE TO RELATED APPLICATION

This application is related to Provisional patent application Ser. No. 60/055,453, filed Aug. 11, 1997, from which priority is claimed under 35 USC §119(e)(1) and which application is incorporated herein by reference in its entirety.

TECHNICAL FIELD

The present invention relates generally to methods for genetically modifying a population of cells with high efficiency and to methods of gene delivery. More particularly, the invention relates to a method for genetically modifying a population of T cells ex vivo.

BACKGROUND OF THE INVENTION

Gene therapy provides a method for transferring a desired gene to a subject with the subsequent in vivo expression thereof. Gene transfer is generally accomplished by genetically modifying the subject's cells or tissues ex vivo, using an appropriate vector, and reintroducing the modified cells into the host. Alternatively, genetic material can be transferred directly into the cells and tissues of the subject.

A number of viral based systems have been used for gene delivery. For example, retroviral systems are known and generally employ packaging lines which have an integrated defective provirus (the "helper") that expresses all of the genes of the virus but cannot package its own genome due to a deletion of the packaging signal, known as the psi ($\psi$) sequence. Thus, the cell line produces empty viral shells. Producer lines can be derived from the packaging lines which, in addition to the helper, contain a viral vector which includes sequences required in cis for replication and packaging of the virus, known as the long terminal repeats (LTRs). The gene of interest can be inserted in the vector and packaged in the viral shells synthesized by the retroviral helper. The recombinant virus can then be isolated and delivered to a subject. (See, e.g., U.S. Pat. No. 5,219,740.)

A critical factor in achieving effective gene transfer is the ability to obtain viral infection of a sufficient proportion of the contacted cells. Often in gene transfers, less than one-third of the cells contacted by a virus ex vivo are effectively modified. Furthermore, large numbers of genetically modified cells are required for most gene delivery applications. Thus, where the efficiency of viral infection is low, the difficulty in obtaining a sufficient number of genetically modified cells can present a limiting step in achieving effective therapy. There thus exists a need for efficient and effective genetic modification of mammalian cells. The present invention satisfies this need and provides related advantages as well.

SUMMARY OF THE INVENTION

A method is provided for producing a population of genetically modified T cells. In the method, an in vitro population of T cells is activated by contacting said population with a CD3 binding agent. Genetic modification is then carried out with the activated T cells by contacting the same with a suitable gene transfer vector. In the practice of the invention, genetic modification is carried out when the cell density of the T cell population is between about $0.1 \times 10^6$ and $5 \times 10^6$.

In various aspects of the invention, the gene transfer vector comprises a promoter operably linked to a first nucleotide sequence capable of being expressed to provide a genetically modified cell with enhanced susceptibility to a selected cytotoxic agent. Thus, the first nucleotide sequence can be a drug susceptibility gene such as a Herpes Simplex Virus thymidine kinase (HSV-tk) gene. Furthermore, the gene transfer vector can comprise a retroviral vector containing one or more nucleotide sequences of interest.

In another embodiment, a method is provided for obtaining a transduction efficiency of 100% or greater in a non-selected population of transduced T cells. The method includes the following steps: (a) providing an in vitro population of T cells; (b) activating the T cells by contacting the T cell population with a CD3 binding agent; and (c) transducing the activated T cells with a retroviral vector at a multiplicity of infection (MOI) of about 3 or greater, wherein transduction is carried out when the cell density of the T cell population is between about $5 \times 10^5$ and $2 \times 10^6$.

In yet another embodiment, a kit is provided for producing a population of transduced T cells. The kit comprises a CD3 binding agent contained in one or more containers, a gene transfer vector contained in one or more containers, ancillary reagents and/or hardware, and instructions for use of the kit.

These and other embodiments of the present invention will readily occur to those of ordinary skill in the art in view of the disclosure herein.

BRIEF DESCRIPTION OF THE FIGURES

FIG. 3 is a map of the retroviral TK vector DAHSVTK9A.

FIG. 4 is a map of the RVV HSV-TK Provector.

DETAILED DESCRIPTION OF THE PREFERRED EMBODIMENTS

Figure 1:
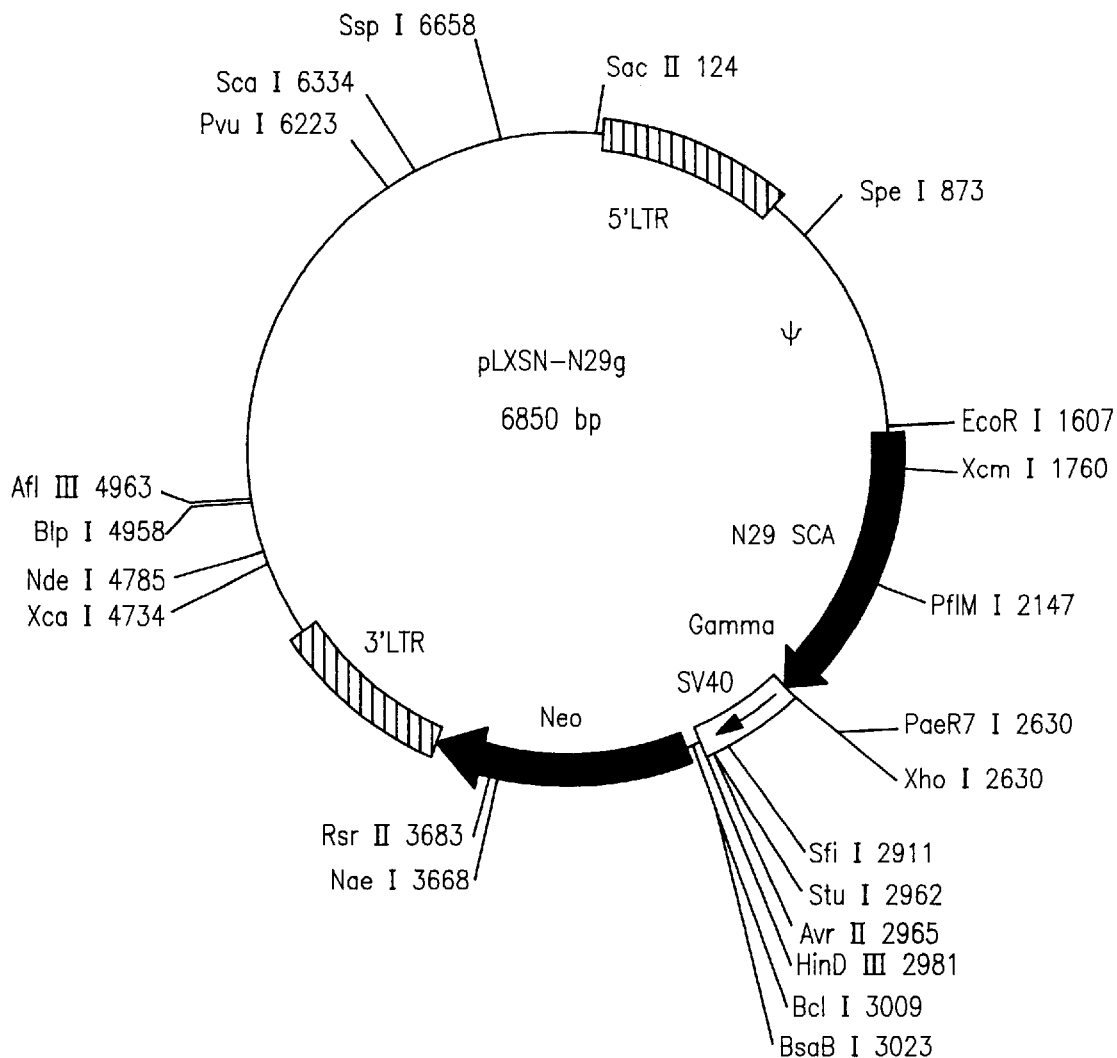
FIG. 1 is a map of the plasmid pLXSN-N29g.

The practice of the present invention will employ, unless otherwise indicated, conventional methods of virology, microbiology, molecular biology, recombinant DNA techniques and immunology within the skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); *Fundamental Virology*, 2nd Edition, vol. I & II (B. N. Fields and D. M. Knipe, eds.); *Methods In Enzymology* (S. Colowick and N. Kaplan, eds., Academic Press, Inc.); and *Handbook of Experimental Immunology*, Vols. I–IV (D. M. Weir and C. C. Blackwell, eds., 1986, Blackwell Scientific Publications)

As used in this specification and the appended claims, the singular forms "a," "an" and "the" include plural references unless the content clearly dictates otherwise.

I. Definitions

In describing the present invention, the following terms will be employed, and are intended to be defined as indicated below.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells.

"T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual,* Cold Spring Harbor Laboratories, New York, Davis et al. (1986) *Basic Methods in Molecular Biology,* Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

The term "transduction" denotes the delivery of a DNA molecule to a recipient cell either in vivo or in vitro, via a replication-defective viral vector, such as a retroviral gene transfer vector.

A recipient cell which has been "genetically modified" has been transfected or transduced, either in vivo or in vitro, with a gene transfer vector containing a DNA molecule of interest.

By "vector," "vector construct," and "gene transfer vector," is meant any nucleic acid construct capable of directing the expression of a gene of interest and which can transfer gene sequences to target cells. Thus, the term includes cloning and expression vehicles, as well as viral vectors.

Transfer of a "suicide gene" (e.g., a drug-susceptibility gene) to a target cell renders the cell sensitive to compounds or compositions that are relatively nontoxic to normal cells. Moolten, F. L. (1994) *Cancer Gene Ther.* 1:279–287. Examples of suicide genes are thymidine kinase of herpes simplex virus (HSV-tk), cytochrome P450 (Manome et al. (1996) *Gene Therapy* 3:513–520), human deoxycytidine kinase (Manome et al. (1996) *Nature Medicine* 2(5):567–573) and the bacterial enzyme cytosine deaminase (Dong et al. (1996) *Human Gene Therapy* 7:713–720). Cells which express these genes are rendered sensitive to the effects of the relatively nontoxic prodrugs ganciclovir (HSV-tk), cyclophosphamide (cytochrome P450 2B1), cytosine arabinoside (human deoxycytidine kinase) or 5-fluorocytosine (bacterial cytosine deaminase). Culver et al. (1992) *Science* 256:1550–1552, Huber et al. (1994) *Proc. Natl. Acad. Sci. U.S.A.* 91:8302–8306.

A "selectable marker" refers to a nucleotide sequence included in a gene transfer vector that has no therapeutic activity, but rather is included to allow for simpler preparation, manufacturing, characterization or testing of the gene transfer vector.

A "specific binding agent" refers to a member of a specific binding pair of molecules wherein one of the molecules specifically binds to the second molecule through chemical and/or physical means.

A "coding sequence" or a sequence which "encodes" a selected molecule, is a nucleic acid molecule which is transcribed (in the case of DNA) and translated (in the case of mRNA) into a polypeptide in vivo when placed under the control of appropriate regulatory sequences.

A "nucleic acid molecule," or "nucleotide sequence" can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

II. Modes of Carrying Out the Invention

The present invention is based on the surprising discovery that a population of T cells can be genetically modified with high efficiency using a vector construct in ex vivo methodologies.

T cells can be isolated from peripheral blood lymphocytes (PBLs) by a variety of procedures known to those skilled in the art. For example, T cell populations can be "enriched" from a population of PBLs through the removal of accessory and B cells. In particular, T cell enrichment can be accomplished by the elimination of non-T cells using anti-MHC class II monoclonal antibodies. Similarly, other antibodies can be used to deplete specific populations of non-T cells. For example, anti-Ig antibody molecules can be used to deplete B cells and anti-MacI antibody molecules can be used to deplete macrophages.

T cells can be further fractionated into a number of different subpopulations by techniques known to those skilled in the art. Two major subpopulations can be isolated based on their differential expression of the cell surface markers CD4 and CD8. For example, following the enrichment of T cells as described above, CD4$^+$ cells can be enriched using antibodies specific for CD4 (see Coligan et al., supra). The antibodies may be coupled to a solid support such as magnetic beads. Conversely, CD8+ cells can be enriched through the use of antibodies specific for CD4 (to remove CD4$^+$ cells), or can be isolated by the use of CD8 antibodies coupled to a solid support. CD4 lymphocytes from HIV-1 infected patients can be expanded ex vivo, before or after transduction as described by Wilson et. al. (1995) *J. Infect. Dis.* 172:88.

Following purification of T cells, a variety of methods of genetic modification known to those skilled in the art can be performed using non-viral or viral-based gene transfer vectors constructed as described herein. For example, one such approach involves transduction of the purified T cell population with vector-containing supernatant cultures derived from vector producing cells. A second approach involves co-cultivation of an irradiated monolayer of vector-producing cells with the purified T cells. A third approach involves a similar co-cultivation approach; however, the purified T cells are pre-stimulated with various cytokines and cultured 48 hours prior to the co-cultivation with the irradiated vector producing cells. Pre-stimulation prior to such transduction increases effective gene transfer (Nolta et al. (1992) *Exp. Hematol.* 20:1065). While not wishing to be bound by a particular theory, the increased level of transduction is attributed to increased proliferation of the T cells necessary for efficient retroviral transduction. Stimulation of these cultures to proliferate also provides increased cell populations for re-infusion into the patient. Subsequent to co-cultivation, T cells are collected from the vector producing cell monolayer, expanded, and frozen in liquid nitrogen.

Gene transfer vectors, containing one or more coding sequences of interest associated with appropriate control elements for delivery to the isolated T cells, can be assembled using known methods.

Selectable markers can also be used in the construction of gene transfer vectors. For example, a marker can be used which imparts to a mammalian cell transduced with the gene transfer vector resistance to a cytotoxic agent. The cytotoxic agent can be, but is not limited to, neomycin, aminoglycoside, tetracycline, chloramphenicol, sulfonamide, actinomycin, netropsin, distamycin A, anthracycline, or pyrazinamide. For example, neomycin phosphotransferase II imparts resistance to the neomycin analogue geneticin (G418).

Non-immunogenic selectable markers are preferred for use herein. "Non-immunogenic" refers to a selectable marker or prodrug activating enzyme that does not cause an undesired immune reaction in the majority of patients when it is administered as part of a gene delivery vehicle. Such genes may be human genes, non-human genes, or mutated human genes that lack sufficient difference from normal human genes (normally less than 10% amino acid sequence difference). Genes that are not of human origin for use herein will not carry epitopes that allow effective presentation of the protein sequence through MHC class I or class II presentation in patients, or may be genes that carry sequences that prevent the effective presentation of otherwise immunogenic epitopes. It is important to note that at least some non-immunogenic selectable markers will be species-specific. For clinical use, non-immunogenic markers will generally be of human origin.

A wide variety of non-immunogenic markers may be expressed by the gene transfer vectors of the present invention. Briefly, such markers may be readily tested for immunogenicity by a variety of assays, including for example, CTL assays for antigens to which the organism has previously generated immunity, and in vitro generation of T-cell response utilizing dendritic cells transduced with the antigen or antigens to which the organism does not have a previously existing response (see Henderson et al. (1996) *Canc. Res.* 56:3763; Hsu et al. (1995) *Nat. Med.* 2:52). CTL assays can be conducted as described in, e.g., International Publication Number WO 91/02805. Another method for ensuring that a marker is non-immunogenic is to administer the marker in a standard skin test such as one utilized to test allergic reactions. It should be noted however, that while the above tests may be utilized in order to ascertain markers which are non-immunogenic within the context of the present invention, a small percentage of patients may nevertheless react against the markers.

Suitable non-immunogenic markers may be obtained from a variety of sources. For example, the marker may be, in its native state, a human enzyme, and thus, by its very nature, non-immunogenic. Similarly, markers from closely related species such as macaques may likewise be non-immunogenic. The marker may be of non-human origin, and can be made non-immunogenic by mutation (e.g., substitution, deletion or insertion). Representative examples of such markers and associated prodrug molecules include alkaline phosphatase and various toxic phosphorylated compounds such as phenolmustard phosphate, doxorubicin phosphate, mitomycin phosphate and etoposide phosphate; β-galactosidase and N-[4-(β-D-galactopyranosyl) benyloxycarbonyl]-daunorubicin; azoreductase and azobenzene mustards; β-glucosidase and amygdalin; β-glucuronidase and phenolmustard-glucuronide and epirubicin-glucuronide; carboxypeptidase A and methotrexate-alanine; cytochrome P450 and cyclophosphamide or ifosfamide; DT diaphorase and 5-(aziridine-1-yl)-2,4,dinitrobenzamide (CB1954) (Cobb et al. (1969) *Biochem. Pharmacol* 18:1519, Knox et al. (1993) *Cancer Metastasis Rev.* 12:195); β-glutamyl transferase and β-glutamyl p-phenylenediamine mustard; nitroreductase and CB1954 or derivatives of 4-nitrobenzyloxycarbonyl; glucose oxidase and glucose; xanthine oxidase and hypoxanthine; and plasmin and peptidyl-p-phenylenediamine-mustard. Non-immunogenic markers may also be made by expressing an enzyme in a compartment of the cell where it is not normally expressed. For example, the enzyme furin, normally expressed in the trans-Golgi, can be expressed on the cell surface. It can then activate drugs that normally may not reach the trans-Golgi.

Alternatively, the exogenous selectable marker can be a protein which is expressed on the surface of a cell such that cells expressing the marker can be physically separated from other cells in a population by immunochemical or receptor-ligand binding methods. Cell surface markers can include cell-adhesive factors, such as the integrins, which modulate cell binding to extracellular matrix proteins.

In one particular embodiment, vectors expressing a suicide gene are provided. Coding sequences for a suicide gene can be obtained using known methods. For example, the coding region and transcriptional termination signals of HSV-I thymidine kinase gene (HSV-TK) can be isolated from plasmid 322TK (McKnight et. al. (1980) *Nuc. Acids Res.* 8:5949) and then cloned into a suitable gene transfer vector.

In other embodiments, vectors expressing human Factor VIII and IX can be provided for use in the treatment of hemophilia. Particularly, vectors expressing a B domain-deleted factor VIII protein are described in the examples below. The B domain separates the second and third A domains of factor VIII in the newly synthesized single-chain molecule. The B domain extends from amino acids 712 to 1648 of the molecule. Wood et al. (1984) *Nature* 312:330–337. Proteolytic activation of factor VIII involves cleavage at specific Arg residues located at positions 372, 740, and 1689. Cleavage of plasma factor VIII by thrombin or Factor Xa at Arg 372 and Arg 1689 are essential for obtaining active factor VIII. Activated factor VIII consists of a calcium-bridged heterodimer comprising amino acids residues 1–372 (containing the A1 domain) and residues 373–740 (containing the A2 domain), and residues 1690–2332 (containing the A3-C1-C2 domain).

An important advantage in using a B domain-deleted factor VIII molecule in the practice of the invention is that the reduced size appears to be less prone to proteolytic degradation and, therefore, no addition of plasma-derived albumin is necessary for stabilization of the final product. The term "B domain deletion" as used herein with respect to factor VIII protein refers to a factor VIII protein in which some or all of the amino acids between residues 711 and 1694 have been deleted, and which still preserves a biologically active factor VIII molecule.

A range of B domain deletions can exist depending on which amino acid residues in the B domain are deleted. One specific B domain deletion, termed "the SQN deletion," exists and has been created by fusing Ser 743 to Gln 1638 (Lind et al. (1995) *Eur. J. Biochem.* 323:19–27, and International Publication No. WO 91/09122). This removes amino acid residues 744 to 1637 from the B domain creating a Ser-Glu-Asn (SQN) link between the A2 and A3 factor VIII domains. When compared to plasma-derived factor VIII, the SQN deletion does not influence the in vivo pharmacokinetics of the factor VIII molecule (Fijnvandraat et. al. (1997) *P.R.Schattauer Vertagsgesellschatt mbH* (Stuttgart) 77:298–302). The terms "Factor VIII SQN deletion" or "SQN deletion" as used herein refer to this deletion and to other deletions which preserve the single S—Q—N tripeptide sequence and which result in the deletion of the amino acids between the two B-domain SQN sequences (See International Publication No. WO 91/09122 for a description of this amino acid sequence).

There are number of other B domain-deleted forms of factor VIII. cDNA's encoding all of these B domain-deleted factor VIII proteins can be inserted into gene transfer vectors using standard molecular biology techniques. For example, cDNA molecules encoding the following factor VIII B domain-deletions can be employed in the practice of the invention: des 797–1562 (Eaton (1986) *Biochemistry* 25:8343); des 760–1639 (LA-FVIII) (Toole (1986) *Proc. Natl. Acad. Sci. U.S.A.* 83:5939); des 771–1666 (FVIII del II: missing one thrombin site) (Meutien (1988) *Prot. Eng.* 2:301); des 747–1560 (Sarver (1987) *DNA* 6:553); des 868–1562 and des 713–1637 (thrombin resistant) (Mertens (1993) *Br. J. Haematol.* 85:133); des 797–1562 (Esmon (1990) *Blood* 76:1593); des 741–1668 (Donath (1995) *Biochem. J.* 312:49); des 748–1648 (partially processed), des 753–1648 (partially processed), des 777–1648 (partially processed), des 744–1637 (FVIII-SQ), des 748–1645 (FVIII-RH), des B-domain +0, 1, 2 Arg (partially processed), desB +3Arg (FVIIIR4), desB +4Arg (FVIIIR5) (Lind (1995) *Eur. J. Biochem.* 232:19); des 741–1689 or des 816–1598 (Langner (1988) *Behring Inst Mitt* 16–25); des 746–1639 (Cheung (1996) *Blood* 88:325a); and des 795–1688 (thrombin sites mutated) (Pipes (1996) *Blood* 88:441a).

Other factor VIII B domain deletions that can be employed herein include, but are not limited to, a B domain deletion in which an IgG hinge region has been inserted (see, e.g., U.S. Pat. No. 5,595,886), and the B domain-deleted factor VIII molecules described in commonly owned U.S. patent application entitled "Methods for Administration of Recombinant Delivery Vehicles for Treatment of Hemophilia and Other Disorders," filed Jun. 4, 1997 as U.S. application Ser. No. 08/869,309, now abandoned, which application is incorporated herein by reference in its entirety.

The full-length factor VIII cDNA can also be inserted into the gene transfer vectors of the invention, such as the cDNA molecule described in International Publication No. WO 96/21035 which is hereby incorporated by reference in its entirety. A variety of Factor VIII deletions, mutations, and polypeptide analogs of Factor VIII also suitable for use herein include, for example, those analogs described in International Publication Nos. WO 97/03193, WO 97/03194, WO 97/03195, and WO 97/03191, all of which are hereby incorporated by reference.

Hemophilia B can also be treated using gene delivery techniques with factor IX-expressing gene transfer vectors. Human factor IX deficiency (Christmas disease or Hemophilia B) affects primarily males because it is transmitted as a sex-linked recessive trait. It affects about 2000 people in the U.S. The human factor IX gene codes for a mature protein of 416 amino acid residues.

Human factor IX cDNA can be obtained, for example, from the plasmid construct pHfIX1 as described by Kurachi et al. (1982) *Proc. Natl. Acad. Sci. U.S.A.* 79:6461–6464. The cDNA sequence can be excised as a PstI fragment of about 1.5 kb and blunt-ended using T4 DNA polymerase. The factor cDNA fragment can then be readily inserted, for example into a suitable restriction site in a vector.

The present invention also can be used in therapy and/or prophylaxis of thrombosis due to APC resistance, and other disorders of thrombosis and hypercoagulation, by providing gene transfer vectors capable of expressing factor V. Blood coagulation consists of a series of sequential activations of circulating serine protease zymogens, culminating in the activation of prothrombin to form thrombin and the subsequent generation of fibrin, the substance of the clot. Two of these reactions, the activation of prothrombin and factor X, require participation of the large proteinaceous cofactors, factors Va and VIIIa, respectively. The serine protease zymogen (Protein C) exerts anticoagulant effect when it is cleaved by thrombin to form activated protein C. Activated protein C (APC) destroys the activity of factors Va and VIIIa through cleavage at specific arginine residues. Genetic deficiencies in protein C or its cofactor, protein S, account for ~5–10% of cases of familial thrombophilia. In 1993, Dahlback described a new form of thrombophilia, called activated protein C resistance (APC resistance) in which added APC failed to prolong the clotting times of patients' plasmas. Dahlback (1993) *Proc. Natl. Acad. Sci. U.S.A.* 90:1004. This was subsequently shown to account for up to 40% of the cases of familial thrombophilia, making it the most common form of inherited disposition to thrombosis (Sun et al. (1994) *Blood* 83:3120). Greater than 95% of APC resistance cases result from a single point mutation in factor V, R506Q (Bertina et al. (1994) *Nature* 369:64, Greengard et al. (1994) *Lancet* 343:1361). This mutation was subsequently found to be present in various healthy European populations at a level of 1–10% (Svensson et al. (1994) *New Engl. J. Med.* 300:517, Griffin et al. (1993) *Blood* 82:1989, Koster et al. *Lancet* 342:1503), and presence/absence of symptoms can vary considerably in a family with numerous homozygotes (Greengard et al. (1995) *New Engl. J. Med.* 331:1559), underscoring the multifactorial nature of thrombotic disease. Rosendaal et al. (1995) *Blood* 85:1504, estimated the relative risk of thrombosis in a heterozygote for APC resistance as seven-fold, and for homozygotes as 80-fold.

Greengard et al. (1995) *Thromb Haemostas* 73:1361(abs) described carrying both a null allele for factor V deficiency and APC resistance. Since these two factor V defects assorted independently, they represent two different factor V alleles. The compound heterozygotes had circulating factor V derived only from the APC resistant factor V allele, and two of the three symptomatic family members had this "pseudohomozygous" genotype. Other family members with only factor V deficiency had no thrombosis. While not wishing to be bound by theory, the risk factor of an APC resistance allele can be compensated in some cases by the mere presence of some normal (APC responsive) factor V. Thus, delivery of normal factor V can be of therapeutic benefit even in the presence of the same amount of resistant factor V, perhaps due to this mechanism.

Thus, nucleotide sequences encoding factor V can be incorporated into a gene transfer vector according to the invention. Factor V cDNA can be obtained from pMT2-V (Jenny (1987) *Proc. Natl. Acad. Sci. U.S.A.* 84:4846, ATCC Deposit No. 40515) by digestion with SalI, and the 7 kb cDNA band excised from agarose gels and cloned into vectors, using standard molecular biology techniques. Either a full-length factor V cDNA, or a B domain deletion or B domain substitution thereof, can be used. B domain deletions of factor V, such as those reported by Marquette (1995) *Blood* 86:3026 and Kane (1990) *Biochemistry* 29:6762, can be made as described by the authors.

Gene transfer vectors can likewise be constructed herein to express antithrombin III for treatment or prophylaxis of hypercoagulable conditions. The central enzyme of the coagulation pathways, thrombin, acts directly through cleavage of fibrinogen to form fibrin, the substance of the clot, or indirectly through positive feedback mechanisms involving activation of other clotting factors. The most commonly used acute-phase anticoagulant used is heparin which augments thrombin inhibition. The major thrombin inhibitor in plasma is antithrombin III (ATIII). The frequency of ATIII deficiency is as high as 1:500 (Tait (1990) *Br. J. Haematol.* 75:141). Although most cases are clinically silent, deficiency may pose a risk factor synergistic with others. Most patients are treated with oral anticoagulants supplemented by ATIII concentrates for surgery or other major trauma (Winter (1981) *Br. J. Haematol.* 49:449–457). Oral anticoagulation is considered an inconvenient and inadequate treatment for hypercoagulable states, while plasma-derived proteins carry the risk of transmittal of infectious agents and other problems. Acquired deficiencies of ATIII are more frequent, such as in premature infants, L-asparaginase therapy for leukemia, DIC, sepsis, nephrotic syndromes, traumatic bleeding, severe burns, malignancies, ARDS, DVT/PE, and enteropathies. Concentrates have been used for animal models of some of these conditions (Emerson (1994) *Blood Coag. Fibrinol.* 5:37). The use of gene therapy to deliver ATIII using the methods described herein can provide useful therapy, particularly in ATIII deficiency states.

Gene transfer vectors expressing ATIII can thus be constructed from the vector pKT218 (Prochownik (1983) *J. Biol. Chem.* 258:8389, ATCC Deposit No. 57224/57225) by excision with PstI. The 1.6 kb cDNA insert can be recovered from agarose gels and cloned into a suitable viral or non-viral vector system.

As described above, protein C is a serine protease zymogen that acts to downregulate the coagulation cascade. Protein C deficiency is associated with increased risk of recurrent thrombosis, purpura fulminans, and warfarin-induced skin necrosis (Bauer, *Disorders of Hemostasis*, Ratnoff & Forbes (Eds), WB Saunders, Philadelphia (1996)). The incidence of heterozygosity is as high as 1/200 (Miletich (1987) *New Engl. J. Med.* 317:991). Although most cases are clinically silent, deficiency may pose a risk factor synergistic with others. Recombinant protein C is administered on a compassionate basis to severely affected homozygotes (Minford (1996) *Br. J. Haematol.* 93:215). Homozygotes and symptomatic heterozygotes could be treated more effectively by gene delivery techniques. In addition, there is evidence to suggest that augmenting levels of activated protein C (APC) could play a major role in prevention of thrombosis in patients with other causes (genetic or acquired) of hypercoagulability. In this regard, Gruber (1992) *Blood* 79:2340, showed that low levels of APC circulate in the plasma of normals, and proposed that basal levels of APC serve to downregulate coagulation in response to low-level prothrombotic signals. The ratio of circulating endogenous APC level to protein C zymogen level was lower in protein C-deficient individuals with a history of thrombosis, than in thrombosis-free relatives, but APC levels are generally proportional to zymogen protein C levels (Espana (1996) *Thrombos Haemostas* 75:56–61). While not wishing to be bound by a particular theory, it may be that gene therapy vectors which express protein C in non-deficient individuals at risk for thrombosis from other causes will have a protective effect in individuals with normal levels of protein C due to this mechanism. An artificial variant of protein C, HPC-FLINQ (Richardson (1992) *Nature* 360:261, Kurz (1997) *Blood* 89:534) was recently described with an enhanced activation profile in the presence of thrombin without the normally required cofactor, thrombomodulin, so that APC was generated in the presence of thrombin levels attained during the clotting of plasma. In addition, HPC-S460A, a second artificial variant of human protein C, has a normal activation profile but a much lowered propensity for subsequent inhibition by plasma serpins. While not wishing to be bound by theory, since binding to serpins is the major mechanism for removal of APC from the circulation, the nonenzymatic anticoagulant activity demonstrated for this variant (Gale (1997) *Prot. Sci.* 6:132) may be preferred due to its having a significantly prolonged plasma half-life upon activation. Yet another approach was taken by Ehrlich (1989) *J. Biol. Chem.* 264:14298, who made a variant of protein C that would become activated during the process of secretion, resulting in secretion of the activated enzyme. In particular, delivery of these variants by the means of gene transfer vectors and the genetic modification methods described herein are useful in reducing thrombosis in individuals at risk thereof.

Thus, gene transfer vectors capable of expressing Protein C can be made using techniques known to those of skill in the art. For example, protein C cDNA can be obtained by restriction enzyme digestion of known vectors containing the same (Foster (1984) *Proc. Natl. Acad. Sci. U.S.A.* 81:4766, Beckmann (1985) *Nucleic Acids Res.* 13:5233). The 1.6 kb cDNA insert can then be recovered from agarose gels and cloned into suitable cloning sites of viral and non-viral vectors under standard conditions.

The normal protein C anticoagulant pathway requires activation by the enzyme thrombin. Thrombin is normally a procoagulant enzyme which cleaves fibrinogen to form fibrin, activates platelets, and performs positive feedback reactions on components of the coagulation cascade. Thrombin activity in the anticoagulant pathway under physiological conditions is dependent upon binding to an endothelial cell surface-bound cofactor, thrombomodulin. Upon binding to this protein, thrombin undergoes a conformational change that greatly reduces it's ability to perform the procoagulant reactions mentioned above, while greatly increasing the rate of activation of protein C zymogen, thus changing specificity from a procoagulant to an anticoagulant enzyme. In accordance with this model, infusion of low levels of thrombin has been shown to be antithrombotic (Gruber (1990) *Circ.* 82:578, Hanson (1993) *J. Clin. Invest.* 92:2003, McBane (1995) *Thromb. Haemostas.* 74:879). Thrombin variants with similar changes in specificity in the absence of thrombomodulin have been developed (Dang (1997) *Nature Biotech.* 15:146, Gibbs (1995) *Nature* 378:413, (1991) *Proc. Natl. Acad. Sci. U.S.A.* 88:7371, Wu (1991) *Proc. Natl.*

Acad. Sci. U.S.A. 88:6775, and Guinto (1995) Proc. Natl. Acad. Sci. U.S.A. 92:11185). Delivery of these variants by the means of gene transfer vectors and the methods of genetic modification described herein is thus useful in reducing thrombosis in individuals at risk thereof.

Gene transfer vectors expressing prothrombin and its variants can be constructed by methods known to those of skill in the art. For example, prothrombin cDNA can be obtained by restriction enzyme digestion of a published vector (Degen (1983) Biochemistry 22:2087). The 1.9 kb cDNA insert can then be recovered from agarose gels and cloned into a suitable vector using the techniques described herein.

Finally, the endothelial cell surface protein, thrombomodulin, is a necessary cofactor for the normal activation of protein C by thrombin. A soluble recombinant form has been described (Parkinson (1990) J. Biol. Chem. 265:12602), which was proposed for use as a clinical therapeutic anticoagulant acting via the protein C pathway. Delivery of this and other variants by the gene transfer vectors and genetic modification methodology of the present invention is therefore useful in reducing thrombosis in individuals at risk.

Gene transfer vector expressing thrombomodulin and its variants can be constructed using techniques known to those of skill in the art. In this regard, thrombomodulin cDNA can be obtained from the vector puc19TM15 (Jackman (1987) Proc. Natl. Acad. Sci. U.S.A. 84:6425, Shirai (1988) J. Biochem. 103:281, Wen (1987) Biochemistry 26:4350, Suzuki (1987) EMBO J. 6:1891, ATCC Deposit No. 61348, 61349) by excision with SalI. The 3.7 kb cDNA insert can be recovered from agarose gels and cloned into a suitable viral or non-viral vector system.

There are a number of proteins useful for treatment of hereditary disorders that can be expressed in vivo by the methods of invention. Many genetic diseases caused by inheritance of defective genes result in the failure to produce normal gene products, for example, thalassemia, phenylketonuria, Lesch-Nyhan syndrome, severe combined immunodeficiency (SCID), hemophilia A and B, cystic fibrosis, Duchenne's Muscular Dystrophy, inherited emphysema and familial hypercholesterolemia (Mulligan et al. (1993) Science 260:926, Anderson et al. (1992) Science 256:808, Friedman et al. (1989) Science 244:1275). Although genetic diseases may result in the absence of a gene product, endocrine disorders, such as diabetes and hypopituitarism, are caused by the inability of the gene to produce adequate levels of the appropriate hormone insulin and human growth hormone respectively.

Gene therapy by the methods of the invention is a powerful approach for treating these types of disorders. This therapy involves the introduction of normal recombinant genes into T cells so that new or missing proteins are produced by the T cells after introduction or reintroduction thereof into a patient. A number of genetic diseases have been selected for treatment with gene therapy, including adenine deaminase deficiency, cystic fibrosis, $\alpha_1$-antitrypsin deficiency, Gaucher's syndrome, as well as non-genetic diseases.

In particular, Gaucher's syndrome is a genetic disorder characterized by a deficiency of the enzyme glucocerebrosidase. This enzyme deficiency leads to the accumulation of glucocerebroside in the lysosomes of all cells in the body. For a review see Science 256:794 (1992) and Scriver et al., The Metabolic Basis of Inherited Disease, 6th ed., vol. 2, page 1677). Thus, gene transfer vectors that express glucocerebrosidase can be constructed for use in the treatment of this disorder. Likewise, gene transfer vectors encoding lactase can be used in the treatment of hereditary lactose intolerance, those expressing AD can be used for treatment of ADA deficiency, and gene transfer vectors encoding $\alpha_1$-antitrypsin can be used to treat $\alpha_1$-antitrypsin deficiency. See Ledley, F. D. (1987) J. Pediatrics 110:157–174, Verma, I. (November 1987) Scientific American pp. 68–84, and International Publication No. WO 95/27512 entitled "Gene Therapy Treatment for a Variety of Diseases and Disorders," for a description of gene therapy treatment of genetic diseases.

Another genetic disorder, familial hypercholesterolemia, is characterized: clinically by a lifelong elevation of low density lipoprotein (LDL), the major cholesterol-transport lipoprotein in human plasma; pathologically by the deposition of LDL-derived cholesterol in tendons, skin and arteries leading to premature coronary heart disease; and genetically by autosomal dominant inherited trait. In heterozygotes (occurring in about 1 in 500 persons worldwide), cells are able to bind cholesterol at about half the rate of normal cells. Heterozygote plasma cholesterol levels show two-fold elevation starting at birth. Homozygotes occur at a frequency of about 1/1 million persons. These individuals have severe cholesterolemia with death occurring usually before age 20. The disease associated with this disorder (Arteriosclerosis) depends on geography, and affects 15.5 per 100,000 individuals in the U.S. (20,000 total) and 3.3 per 100,000 individuals in Japan. Gene transfer vectors expressing the LDL receptor for treatment of disorders manifesting with elevated serum LDL can thus be constructed by techniques known to those of skill in the art.

In still further embodiments of the invention, nucleotide sequences which can be incorporated into a gene transfer vector include, but are not limited to, proteins associated with enzyme-deficiency disorders, such as the cystic fibrosis transmembrane regulator (see, for example, U.S. Pat. No. 5,240,846 and Larrick et al. (1991) Gene Therapy Applications of Molecular Biology, Elsevier, New York and adenosine deaminase (ADA) (see U.S. Pat. No. 5,399,346); growth factors, or an agonist or antagonist of a growth factor (Bandara et al. (1992) DNA and Cell Biology, 11:227); one or more tumor suppressor genes such as p53, Rb, or C-CAMI (Kleinerman et al. (1995) Cancer Research 55:2831); a molecule that modulates the immune system of an organism, such as a HLA molecule (Nabel et al. (1993) Proc. Natl. Acad. Sci. U.S.A. 90:11307); a ribozyme (Larsson et al. (1996) Virology 219:161); a peptide nucleic acid (Hirshman et al. (1996) J. Invest. Med. 44:347); an antisense molecule (Bordier et al. (1995) Proc. Natl. Acad. Sci. U.S.A. 92:9383) which can be used to down-regulate the expression or synthesis of aberrant or foreign proteins, such as HIV proteins or a wide variety of oncogenes such as p53 (Hesketh, The Oncogene Facts Book, Academic Press, New York, (1995); a biopharmaceutical agent or antisense molecule used to treat HIV-infection, such as an inhibitor of p24 (Nakashima et al. (1994) Nucleic Acids Res. 22:5004); or reverse-transcriptase (see, Bordier, supra).

Other proteins of therapeutic interest can be expressed in vivo by gene transfer vectors using the methods of the invention. For instance sustained in vivo expression of tissue factor inhibitory protein (TFPI) is useful for treatment of conditions including sepsis and DIC and in preventing reperfusion injury. (See International Publications Nos. WO 93/24143, WO 93/25230 and WO 96/06637). Nucleic acid sequences encoding various forms of TFPI can be obtained, for example, as described in U.S. Pat. Nos. 4,966,852;

5,106,833; and 5,466,783, and incorporated into the gene transfer vectors described herein.

Erythropoietin (EPO) and leptin can also be expressed in vivo from genetically modified T cells according to the methods of the invention. For instance EPO is useful in gene therapy treatment of a variety of disorders including anemia (see International Publication No. WO 95/13376 entitled "Gene Therapy for Treatment of Anemia"). Sustained delivery of leptin by the methods of the invention is useful in treatment of obesity. See International Publication No. WO 96/05309 for a description of the leptin gene and the use thereof in the treatment of obesity.

A variety of other disorders can also be treated by the methods of the invention. For example, sustained in vivo systemic production of apolipoprotein E or apolipoprotein A from genetically modified T cells can be used for treatment of hyperlipidemia (see Breslow et al. (1994) *Biotechnology* 12:365). Sustained production of angiotensin receptor inhibitor (Goodfriend et al. (1996) *N. Engl. J. Med.* 334:1469) can be provided by the methods described herein. As yet an additional example, the long term in vivo systemic production of angiostatin is useful in the treatment of a variety of tumors. (See O'Reilly et al. (1996) *Nature Med.* 2:689).

In other embodiments, the present gene transfer vectors can be constructed to encode a cytokine or other immunomodulatory molecule. For example, nucleic acid sequences encoding native IL-2 and gamma-interferon can be obtained as described in U.S. Pat. No. Nos. 4,738,927 and 5,326,859, respectively, while useful muteins of these proteins can be obtained as described in U.S. Pat. No. 4,853,332. Nucleic acid sequences encoding the short and long forms of mCSF can be obtained as described in U.S. Pat. Nos. 4,847,201 and 4,879,227, respectively. In particular aspects of the invention, retroviral vectors expressing cytokine or immunomodulatory genes can be produced as described herein and in International Application No. PCT US 94/02951, entitled "Compositions and Methods for Cancer Immunotherapy."

Examples of suitable immunomodulatory molecules for use herein include the following: IL-1 and IL-2 (Karupiah et al. (1990) *J. Immunology* 144:290–298, Weber et al. (1987) *J. Exp. Med.* 166:1716–1733, Gansbacher et al. (1990) *J. Exp. Med.* 172:1217–1224, and U.S. Pat. No. 4,738,927); IL-3 and IL-4 (Tepper et al. (1989) *Cell* 57:503–512, Golumbek et al. (1991) *Science* 254:713–716, and U.S. Pat. No. 5,017,691); IL-5 and IL-6 (Brakenhof et al. (1987) *J. Immunol.* 139:4116–4121, and International Publication No. WO 90/06370); IL-7 (U.S. Pat. No. 4,965,195); IL-8, IL-9, IL-10, IL-11, IL-12, and IL-13 (*Cytokine Bulletin,* Summer 1994); IL-14 and IL-15; alpha interferon (Finter et al. (1991) *Drugs* 42:749–765, U.S. Pat. Nos. 4,892,743 and 4,966,843, International Publication No. WO 85/02862, Nagata et al. (1980) *Nature* 284:316–320, Familletti et al. (1981) *Methods in Enz.* 78:387–394, Twu et al. (1989) *Proc. Natl. Acad. Sci. U.S.A.* 86:2046–2050, and Faktor et al. (1990) *Oncogene* 5:867–872); beta-interferon (Seif et al. (1991) *J. Virol.* 65:664–671); gamma-interferons (Radford et al. (1991) *The American Society of Hepatology* 20082015, Watanabe et al. (1989) *Proc. Natl. Acad. Sci. U.S.A.* 86:9456–9460, Gansbacher et al. (1990) *Cancer Research* 50:7820–7825, Maio et al. (1989) *Can. Immunol. Immunother.* 30:34–42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942–951); CD3 (Krissanen et al. (1987) *Immunogenetics* 26:258–266); ICAM-1 (Altman et al. (1989) *Nature* 338:512–514, Simmons et al. (1988) *Nature* 331:624–627); ICAM-2, LFA-1, LFA-3 (Wallner et al. (1987) *J. Exp. Med.* 166:923–932); MHC class I molecules, MHC class II molecules, B7.1-.3, $\beta_2$-microglobulin (Parnes et al. (1981) *Proc. Natl. Acad. Sci. U.S.A.* 78:2253–2257); chaperones such as calnexin; and MHC-linked transporter proteins or analogs thereof (Powis et al. (1991) *Nature* 354:528–531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection (ATCC, Manassas, Va.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC Deposit No. 39656 (which contains sequences encoding TNF), ATCC Deposit No. 20663 (which contains sequences encoding alpha-interferon), ATCC Deposit Nos. 31902, 31902 and 39517 (which contain sequences encoding beta-interferon), ATCC Deposit No. 67024 (which contains a sequence which encodes Interleukin-1b), ATCC Deposit Nos. 39405, 39452, 39516, 39626 and 39673 (which contain sequences encoding Interleukin-2), ATCC Deposit Nos. 59399, 59398, and 67326 (which contain sequences encoding Interleukin-3), ATCC Deposit No. 57592 (which contains sequences encoding Interleukin-4), ATCC Deposit Nos. 59394 and 59395 (which contain sequences encoding Interleukin-5), and ATCC Deposit No. 67153 (which contains sequences encoding Interleukin-6).

Plasmids containing cytokine genes or immunomodulatory genes can be digested with appropriate restriction enzymes, and DNA fragments containing the particular gene of interest can be inserted into the gene transfer vector using standard molecular biology techniques. (See, e.g., Sambrook et al., supra., or Ausbel et al. (eds) *Current Protocols in Molecular Biology,* Greene Publishing and Wiley-Interscience, New York (1987)). In particular, retroviral vectors expressing cytokine and immunomodulatory molecules can be constructed as described in International Publication Nos. WO 94/02951 and WO 96/21015, both of which are incorporated by reference in their entirety.

A variety of known polypeptide hormones and growth factors can also be used in the instant gene transfer vectors to provide for therapeutic long-term expression of these proteins. Exemplary hormones, growth factors and other proteins which are useful for long term expression by the vectors of the invention are described, for example, in European Publication No. 0437478B1, entitled "Cyclodextrin-Peptide Complexes." Nucleic acid sequences encoding a variety of hormones can be used, including those encoding human growth hormone, insulin, calcitonin, prolactin, follicle stimulating hormone (FSH), luteinizing hormone (LH), human chorionic gonadotropin (HCG), and thyroid stimulating hormone (TSH). A variety of different forms of IGF-1 and IGF-2 growth factor polypeptides are also well known the art and can be incorporated into gene transfer vectors for long term expression in vivo. See, e.g., European Patent No. 0123228B1, published for grant Sep. 19, 1993, entitled "Hybrid DNA Synthesis of Mature Insulin-like Growth Factors." As an additional example, the long term in vivo expression of different forms of fibroblast growth factor can also be effected by the methods of invention. See, e.g., U.S. Pat. Nos. 5,464,774, 5,155,214, and 4,994,559 for a description of different fibroblast growth factors.

In particular embodiments, the gene transfer vectors of the present invention may include a suicide gene and an ancillary nucleotide sequence which can be expressed to provide immune accessory molecules. As utilized herein, the phrase "immune accessory molecules" refers to molecules which can either increase or decrease the recognition, presentation or activation of an immune response (either cell-mediated or humoral). Representative examples of immune accessory molecules are described above.

When the gene transfer vectors described herein direct the expression of more than one heterologous sequence, such multiple sequences may be controlled either by a single promoter, or preferably, by additional secondary promoters (e.g., Internal Ribosome Binding Sites or "IRBS").

Polynucleotide sequences coding for the above-described molecules can be obtained using recombinant methods, such as by screening cDNA and genomic libraries from cells expressing the gene, or by deriving the gene from a vector known to include the same. For example, plasmids which contain sequences that encode altered cellular products may be obtained from a depository such as the ATCC, or from commercial sources such as Advanced Biotechnologies (Columbia, Md.). Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences for use with the present invention may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also *PCR Technology: Principles and Applications for DNA Amplification*, Erlich (ed.), Stockton Press, 1989)) using oligonucleotide primers complementary to sequences on either side of desired sequences. In particular, a double stranded DNA is denatured by heating in the presence of heat-stable Taq polymerase, sequence-specific DNA primers, and ATP, CTP, GTP and TTP. Double-stranded DNA is produced when synthesis is complete. This cycle may be repeated many times, resulting in a factorial amplification of the desired DNA.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. In general, one will select preferred codons for the intended host in which the sequence will be expressed. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Next, one or more coding sequences can be inserted into a vector which includes control sequences operably linked to the desired coding sequence(s), and which allow for in vivo expression in the targeted host species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the constructs for use with the present invention.

Enhancer elements may also be used herein to increase expression levels of the vector constructs. Examples include the SV40 early gene enhancer, as described in Dijkema et al. (1985) *EMBO J.* 4:761, the enhancer/promoter derived from the long terminal repeat (LTR) of the Rous Sarcoma Virus, as described in Gorman et al. 91982) *Proc. Natl. Acad. Sci. U.S.A.* 79:6777 and elements derived from human CMV, as described in Boshart et al. (1985) *Cell* 41:521, such as elements included in the CMV intron A sequence.

A number of viral based systems have been developed for use as gene transfer vectors for mammalian host cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems have been described and will find use with the present invention, including, for example, those described in (U.S. Pat. No. 5,219,740; Miller et al. (1989) *BioTechniques* 7:980; Miller, A. D. (1990) *Human Gene Therapy* 1:5; Scarpa et al. (1991) *Virology* 180:849; Burns et al. (1993) *Proc. Natl. Acad. Sci. U.S.A.* 90:8033; Boris-Lawrie et al. (1993) *Cur. Opin. Genet. Develop.* 3:102; GB 2200651; EP 0415731; EP 0345242; WO 89/02468; WO 89/05349; WO 89/09271; WO 90/02806; WO 90/07936; WO 90/07936; WO 94/03622; WO 93/25698; WO 93/25234; WO 93/11230; WO 93/10218; WO 91/02805; in U.S. Pat. Nos. 5,219,740; 4,405,712; 4,861,719; 4,980,289 and 4,777,127; in U.S. Ser. No. 07/800,921; and in Vile (1993) *Cancer Res* 53:3860–3864; Vile (1993) *Cancer Res* 53:962–967; Ram (1993) *Cancer Res* 53:83–88; Takamiya (1992) *J Neurosci Res* 33:493–503; Baba (1993) *J Neurosurg* 79:729–735; Mann (1983) *Cell* 33:153; Cane (1984) *Proc Natl Acad Sci U.S.A.* 81;6349; and Miller (1990) *Human Gene Therapy* 1. Retroviral gene transfer vectors are preferred in the practice of the invention.

Retroviral gene transfer vectors used in the practice of the present invention may be readily constructed from a wide variety of retroviruses, including for example, B, C, and D type retroviruses as well as spumaviruses and lentiviruses (see, e.g., *RNA Tumor Viruses,* Second Edition, Cold Spring Harbor Laboratory, 1985). Briefly, retroviruses have been classified according to their morphology as seen under electron microscopy. Type "B" retroviruses appear to have an eccentric core, while type "C" retroviruses have a central core. Type "D" retroviruses have a morphology intermediate between type B and type C retroviruses. Representative examples of suitable retroviruses include, for example, those described in *RNA Tumor Viruses*, at pages 2–7, as well as a variety of xenotropic retroviruses (e.g., NZB-X1, NZB-X2 and NZB9-1 (see O'Neill et al. (1985) *J. Vir.* 53:100–106)) and polytropic retroviruses (e.g., MCF and MCF-MLV (see Kelly et al. (1983) *J. Vir.* 45(1):291–298)). Such retroviruses may be readily obtained from depositories or collections such as the American Type Culture Collection ("ATCC"; Manassas, Va.), or isolated from known sources using commonly available techniques.

Particularly preferred retroviruses for the preparation or construction of retroviral gene transfer vectors of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Gibbon Ape Leukemia Virus, Feline Leukemia Virus, Reticuloendotheliosis virus and Rous Sarcoma Virus. Particularly preferred Murine Leukemia Viruses include 4070A and 1504A (Hartley et al. (1976) *J. Virol.* 19:19–25), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Particularly preferred Rous Sarcoma Viruses include Bratislava, Bryan high titer (e.g., ATCC Nos. VR-334, VR-657, VR-726, VR-659, and VR-728), Bryan standard, Carr-Zilber, Engelbreth-Holm, Harris, Prague (e.g., ATCC Nos. VR-772, and 45033), and Schmidt-Ruppin (e.g., ATCC Nos. VR-724, VR-725, VR-354).

Any of the above retroviruses may be readily utilized in order to assemble or construct retroviral gene transfer vectors given the disclosure provided herein, and standard recombinant techniques (e.g., Sambrook et al., supra; Kunkle (1985) *Proc. Natl. Acad. Sci. U.S.A.* 82:488). Within certain embodiments of the invention, portions of the retroviral gene transfer vectors may be derived from different retroviruses. For example, retroviral vector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Retroviral vector constructs can also be provided comprising a 5' LTR, a tRNA binding site, a packaging signal, one or more heterologous sequences, an origin of second strand DNA synthesis and a 3' LTR, wherein the vector construct lacks gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus due to their precise duplication at either end of the genome. As utilized herein, a 5' LTR is understood to include a 5' promoter element and sufficient LTR sequence to allow reverse transcription and integration of the DNA form of the vector. The 3' LTR includes a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location immediately downstream from the 5' LTR. Similarly, the origin of second strand DNA synthesis is important for the second strand DNA synthesis of a retrovirus. This region, which is also referred to as the poly-purine tract, is located immediately upstream of the 3' LTR.

In addition to a 5' and 3' LTR, tRNA binding site, and origin of second strand DNA synthesis, the retroviral gene transfer vectors may further comprise a packaging signal, as well as one or more heterologous sequences, each of which is discussed in more detail below.

For example, retroviral gene transfer vectors can be provided which lack both gag/pol and env coding sequences. As an illustration, construction of retroviral gene transfer vectors which lack gag/pol or env sequences may be accomplished by preparing vector constructs which lack an extended packaging signal. As utilized herein, the phrase "extended packaging signal" refers to a sequence of nucleotides beyond the minimum core sequence which is required for packaging. The sequence allows increased viral titer due to enhanced packaging. As an example, for the Murine Leukemia Virus MOMLV, the minimum core packaging signal is encoded by the sequence beginning from the end of the 5' LTR through the PstI site. The extended packaging signal of MOMLV includes the sequence beyond nucleotide 567 through the start of the gag/pol gene (nucleotide 621), and beyond nucleotide 1560. Thus, retroviral gene transfer vectors which lack extended packaging signal may be constructed from the MOMLV by deleting or truncating the packaging signal prior to nucleotide 567.

Other retroviral gene transfer vectors can be provided wherein the packaging signal that extends into, or overlaps with, retroviral gag/pol sequence is deleted or truncated. For example, in the representative case of MOMLV, the packaging signal is deleted or truncated prior to the start of the gag/pol gene.

Retroviral gene transfer vectors can also be provided to include a packaging signal that extends beyond the start of the gag/pol gene. When such retroviral vector constructs are utilized, it is preferable to use packaging cell lines for the production of recombinant viral particles wherein the 5' terminal end of the gag/pol gene in a gag/pol expression cassette has been modified to contain codons which are degenerate for gag.

Yet further retroviral vector constructs can be provided which comprise a 5' LTR, a tRNA binding site, a packaging signal, an origin of second strand DNA synthesis and a 3' LTR, wherein the vector construct does not contain a retroviral nucleic acid sequence upstream of the 5' LTR. These vector constructs do not contain a env coding sequence upstream of the 5' LTR.

Retroviral gene transfer vectors can also be provided which comprise a 5' LTR, a tRNA binding site, a packaging signal, an origin of second strand DNA synthesis and a 3' LTR, wherein the vector does not contain a retroviral packaging signal sequence downstream of the 3' LTR. As utilized herein, the term "packaging signal sequence" is understood to mean a sequence sufficient to allow packaging of the RNA genome.

Packaging cell lines suitable for use with the above described retroviral gene transfer vector constructs may be readily prepared (see U.S. application Ser. No. 08/240,030, filed May 9, 1994, now abandoned; see also U.S. application Ser. No. 07/800,921, filed Nov. 27, 1991, now abandoned), and utilized to create producer cell lines (also termed vector cell lines or "VCLS") for the production of recombinant vector particles.

A number of viral vector systems other than those based on retroviruses are known in the art and can be used in the practice of the invention. Since the viral vector systems are used to provide therapeutically useful modified cells, the viral vector systems are preferably genetically modified to render them non-lytic.

A number of adenovirus vectors (Ad vectors) have been described and can be used with the present invention. See, e.g., Haj-Ahmad et al. (1986) *J. Virol.* 57:267; Bett et al. (1993) *J. Virol.* 67:5911; Mittereder et al. (1994) *Human Gene Therapy* 5:717; Seth et al. (1994) *J. Virol.* 68:933; Barr et al. (1994) *Gene Therapy* 1:51; Berkner, K. L. (1988) *BioTechniques* 6:616; and Rich et al. (1993) *Human Gene Therapy* 4:461.

Prototype recombinant adenovirus vectors are generally deleted in the early region one (E1a/E1b, or E1) region, rendering them replication-defective. Following insertion of a nucleotide sequence of interest into the deleted region, propagation of the recombinant E1-deleted adenovirus vector is accomplished in 293 cells, a complementing human embryonic kidney cell line stably transformed with the Ad E1 region, which provides the Ad E1 region gene products in trans. Recombinant Ad vectors generated in this fashion can yield preparations with titers between $10^{11}$ to $10^{13}$ particles/ml (reviewed in Berkner (1988) *BioTechniques* 6:616–629). However, there are several drawbacks to this prototype Ad vector system, including: (1) size restriction of heterologous genetic material to approximately 4.5 to 5.0 kb or less; and (2) partial replication competence of the E1-deleted Ad vectors (Rich (1993) *Hum. Gen. Ther.* 4:461–476). This later point arises in part to a complementing "E1-like activity" that is expressed in human cells, and results in the expression of other viral gene products present in these vectors, including the highly immunogenic, "late," or structural gene products (e.g. penton protein). As a result of immune responses of the recipient to Ad-specific proteins expressed by the E1-deleted vectors, expression of the heterologous gene, or transgene can be transient and associated with the development of pathology at the site of gene transfer.

Thus, second generation Ad vectors have sought to further "cripple" the capacity of the vector to replicate and express viral-specific gene products, and to increase the capacity of heterologous genetic material. Such vectors have been of three types: (1) E1 and E3 genes deleted (Bett (1994) *Proc. Natl. Acad. Sci. U.S.A.* 91:8802–8806); (2) E1 and E4 genes deleted (Wang (1995) *Gene Ther.* 2:775–783); and (3) deletion of all Ad viral genes, or "gutless" (Fisher (1996) *Virology* 217:11–22, Hardy (1996) *J. Virol.* 71:1842–1849, and Kochanek (1996) *Proc. Natl. Acad. Sci. U.S.A.* 93:5731–5736). The duration of transgene expression in animals inoculated with these second generation recombinant adenovirus vectors has been dramatically increased as a result of the mitigation of the recipient's immune response to the Ad vectors.

As expected, increased deletion of viral-specific genes in the second generation Ad vectors has also resulted in an increased capacity for heterologous genetic material, thus extending the usefulness of this system for application to human gene transfer. This capacity for heterologous genetic material is approximately 8 kb in the E1/E3 and E1/E4 vectors, and is greater than 30 kb for the "gutless" Ad vectors, permitting the insertion of entire genes, including relevant gene expression control regions.

Generation of recombinant Ad vectors, including the E1/E3, E1/E4, and "gutless" vectors, can be accomplished according to methods well-known to those skilled in the art. For example: (1) nucleotide sequences of interest can be inserted into plasmid pBHG11 (Bett (1994) *Proc. Natl. Acad. Sci. U.S.A.* 91:8802–8806), to generate recombinant E1/E3-deleted Ad vectors after transfection of 293 cells and subsequent intracellular homologous recombination; (2) nucleotide sequences of interest can be first substituted into the E1 region of any of a variety of E1-deleted Ad vectors and co-transfected with ClaI digested H5d11014, and recombinant E1/E4-deleted Ad vectors generated after transfection of 293-E4 cells (Wang (1995) *Gene Ther.* 2:775–783), and subsequent intracellular homologous recombination; and (3) the nucleotide sequences of interest can first be inserted into the ArAd plasmid (Fisher (1996) *Virology* 217:11–22), along with appropriate amounts of "stuffer" sequence derived from, for example, bacteriophage lambda DNA, to permit efficient packaging of recombinant "gutless" adenovirus vector genomes, transfected onto 293 cells and infected with H5.CBALP helper virus (Yang (1995) *Virology* 69:2004–2015). Purification of recombinant "gutless" adenovirus vector particles from helper virus can be accomplished, for example, by centrifugation over a cesium gradient, as a result of a buoyant density lower than that of helper virus.

Additionally, various adeno-associated virus (AAV) vector systems have been developed for gene delivery and find use herein. AAV vectors can be readily constructed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); commonly owned provisional U.S. patent application Ser. No. 60/025649; Lebkowski et al. (1988) *Molec. Cell. Biol.* 8:3988; Vincent et al. (1990) *Vaccines* 90 (Cold Spring Harbor Laboratory Press); Carter, B. J. (1992) *Current Opinion in Biotechnology* 3:533; Muzyczka, N. (1992) *Current Topics in Microbiol. and Immunol.* 158:97; Kotin, R. M. (1994) *Human Gene Therapy* 5:793; Shelling et al. (1994) *Gene Therapy* 1:165; and Zhou et al. (1994) *J. Exp. Med.* 179:1867.

Additional viral vectors which will find use for delivering the nucleic acid molecules encoding the nucleotide sequences of interest include those derived from the pox family of viruses, including vaccinia virus and avian poxvirus. By way of example, vaccinia virus recombinants expressing the genes can be constructed as follows. DNA encoding the particular gene is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene into the viral genome. The resulting TK⁻ recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al. (1993) *J. Biol. Chem.* 268:6866 and Wagner et al. (1992) *Proc. Natl. Acad. Sci. U.S.A.* 89:6099, can also be used for gene delivery.

Members of the Alphavirus genus, such as but not limited to vectors derived from the Sindbis and Semliki Forest viruses, will also find use as gene delivery vectors for delivering a nucleotide sequence of interest. For a description of Sinbus-virus derived vectors useful for the practice of the instant methods. See, e.g., Dubensky et al. (1996) *J. Virol.* 70:508; and International Publication Nos. WO 95/07995 and WO 96/17072.

A number of non-viral based gene delivery systems have also been developed for use as gene transfer vectors for mammalian host cells including, for example, nucleic acid expression vectors; polycationic condensed DNA linked or unlinked to killed adenovirus alone (see e.g., U.S. patent application Ser. No. 08/366,787, filed Dec. 30, 1994, now abandoned, and Curiel (1992) *Hum. Gene Ther.* 3:147–154); ligand linked DNA (see Wu (1989) *J. Biol. Chem.* 264:16985–16987); eukaryotic cell delivery vehicles cells (see U.S. patent application Ser. No. 08/240,030, filed May 9, 1994, now abandoned, and U.S. patent application Ser. No. 08/404,796); deposition of photopolymerized hydrogel materials; hand-held gene transfer particle gun (see, e.g., U.S. Pat. No. 5,149,655); ionizing radiation (e.g., as described in U.S. Pat. No. 5,206,152 and in International Publication No. WO 92/11033); nucleic charge neutralization or fusion with cell membranes. Additional approaches are described in Philip (1994) *Mol. Cell Biol.* 14:2411–2418, and in Woffendin (1994) *Proc. Natl. Acad. Sci. U.S.A.* 91:1581–1585.

Particle mediated gene transfer may be employed with non-viral based systems, for example, see U.S. provisional application No. 60/023,867. Briefly, the sequence of interest can be inserted into conventional gene transfer vectors containing suitable control sequences for high level expression, and then be incubated with synthetic gene transfer molecules such as polymeric DNA-binding cations like polylysine, protamine, and albumin, linked to cell targeting ligands such as asialoorosomucoid (e.g., as described in Wu et al. (1987) *J. Biol. Chem.* 262:4429–4432), insulin (e.g., as described in Hucked (1990) *Biochem. Pharmacol.* 40:253–263), galactose (e.g., as described in Plank (1992) *Bioconjugate Chem.* 3:533–539), lactose or transferrin.

Naked DNA delivery techniques may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that act as vehicles for gene transfer vectors are described in U.S. Pat. No. 5,422,120, International Publication Nos. WO 95/13796, WO 94/23697, and WO 91/144445, and in European Patent Publication No. 524, 968. As described in U.S. provisional application No. 60/023,867, nucleic acid sequences can be inserted into vectors having control sequences suitable for high level expression, and then incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery techniques suitable for use herein include mechanical delivery systems such as the approach described in Woffendin et al. (1994) *Proc. Natl. Acad. Sci. U.S.A.* 91:11581–11585. Moreover, the coding sequence can be delivered through deposition of photopolymerized hydrogel materials. Other conventional methods for gene delivery that can be used include, for example, use of hand-held gene transfer particle gun, as described in U.S. Pat. No. 5,149,655; and ionizing radiation for activating transferred gene, as described in U.S. Pat. No. 5,206,152 and International Publication No. WO 92/11033.

Exemplary liposome and polycationic gene delivery vehicles are those described in U.S. Pat. Nos. 5,422,120 and 4,762,915, in International Publication Nos. WO 95/13796, WO 94/23697, and WO 91/14445, in European Patent Publication No. 524,968 and in Starrier, *Biochemistry*, pp 236–240 (1975) W.H. Freeman, San Francisco; Shokai (1980) *Biochem. Biophys. Acct.* 600:1; Bayer (1979) *Biochem. Biophys. Acct.* 550:464; Rivet (1987) *Meth. Enzymol.* 149:119; Wang (1987) *Proc. Natl. Acad. Sci. U.S.A.* 84:7851; Plant (1989) *Anal. Biochem.* 176:420.

Once produced, the above-described gene transfer vectors are used to genetically modify a population of T cells isolated as described herein. If a retroviral gene transfer vector is used, a population of cultured T cells is first activated by stimulating the cells to the part of S-phase which is most receptive to transfection. The first quarter to half of S-phase is optimal for retroviral transduction. Other methods of enhancing a cell's receptivity to viral vector transduction include varying the multiplicity of infection, depleting ions such as phosphate, adding polycations such as protamine sulfate, adjusting the contact time, temperature, pH, and centrifuging the cells and viruses together.

In the practice of the invention, T-lymphocytes are preferably activated by contacting them with a CD3-binding agent such as the monoclonal antibody OKT-3. A CD3-binding agent is a ligand which binds to the CD3 molecule on the surface of cells. The ligand can be an antibody, such as OKT-3, which can cross-link two or more CD3 molecules. Such cross-linking can be responsible for the proliferation and activation of CD3-bearing cells such as T-lymphocytes. The activation of T-lymphocytes by CD3-binding agents is increased by adjusting certain factors such as binding agent concentration, time of contact, number of cells, temperature of contact, and the binding agent's affinity, avidity, and efficacy of activating the cells.

The T cells can also be maintained in a medium containing at least one type of growth factor prior to being selected. A variety of growth factors are known in the art which sustain the growth of a particular cell type. Examples of such growth factors are cytokine mitogens such as rIL-2, IL-10, IL-12, and IL-15, which promote growth and activation of lymphocytes. Certain types of cells are stimulated by other growth factors such as hormones, including human chorionic gonadotropin (hCG) and human growth hormone. The selection of an appropriate growth factor for a particular cell population is readily accomplished by one of skill in the art.

For example, white blood cells such as differentiated progenitor and stem cells are stimulated by a variety of growth factors. More particularly, IL-3, IL-4, IL-5, IL-6, IL-9, GM-CSF, M-CSF, and G-CSF, produced by activated $T_H$ and activated macrophages, stimulate myeloid stem cells, which then differentiate into pluripotent stem cells, granulocyte-monocyte progenitors, eosinophil progenitors, basophil progenitors, megakaryocytes, and erythroid progenitors. Differentiation is modulated by growth factors such as GM-CSF, IL-3, IL-6, IL-11, and EPO.

Pluripotent stem cells then differentiate into lymphoid stem cells, bone marrow stromal cells, T cell progenitors, B cell progenitors, thymocytes, $T_H$ Cells, $T_C$ cells, and B cells. This differentiation is modulated by growth factors such as IL-3, IL-4, IL-6, IL-7, GM-CSF, M-CSF, G-CSF, IL-2, and IL-5.

Granulocyte-monocyte progenitors differentiate to monocytes, macrophages, and neutrophils. Such differentiation is modulated by the growth factors GM-CSF, M-CSF, and IL-8. Eosinophil progenitors differentiate into eosinophils. This process is modulated by GM-CSF and IL-5.

The differentiation of basophil progenitors into mast cells and basophils is modulated by GM-CSF, IL-4, and IL-9. Megakaryocytes produce platelets in response to GM-CSF, EPO, and IL-6. Erythroid progenitor cells differentiate into red blood cells in response to EPO.

Thus, during activation by the CD3-binding agent, T cells can also be contacted with a mitogen, for example a cytokine such as IL-2. In particularly preferred embodiments, the IL-2 is added to the population of T cells at a concentration of about 50 to 100 μg/ml. Activation with the CD3-binding agent can be carried out for 2 to 4 days.

Once suitably activated, the T cells are genetically modified by contacting the same with a suitable gene transfer vector under conditions that allow for transfection of the vectors into the T cells. Genetic modification is carried out when the cell density of the T cell population is between about $0.1 \times 10^6$ and $5 \times 10^6$, preferably between about $0.5 \times 10^6$ and $2 \times 10^6$. Although a number of suitable viral and nonviral-based gene transfer vectors have been described for use herein, the invention is hereafter exemplified by transduction of the T cells using a viral-based vector system.

Transduction with a gene transfer vector is generally carried out with a viral vector at a multiplicity of infection (MOI) of about 3 or greater.

In one embodiment, the T cells are washed after activation with the CD3-binding agent, and then re-seeded in cell culture at a cell density of about $5 \times 10^5$.

In another particular embodiment, the gene transfer vector contains a promoter operably linked to a first nucleotide sequence that is capable of being expressed in a transduced cell to provide the cell with enhanced susceptibility to a selected cytotoxic agent. Preferably, the first nucleotide sequence is a suicide gene, such as the herpes simplex virus thymidine kinase (HSV-tk) gene. The gene transfer vector can also include a selectable marker. A number of suitable selectable markers can be used in the practice of the invention, such as those which provide a transduced cell with resistance to a selected cytotoxic agent. One particular selectable marker for use herein is neomycin phosphotransferase II. Other markers useful herein include cell surface markers such as alkaline phosphatase, nerve growth factor, or any other suitable membrane-associated moiety.

Figure 2:
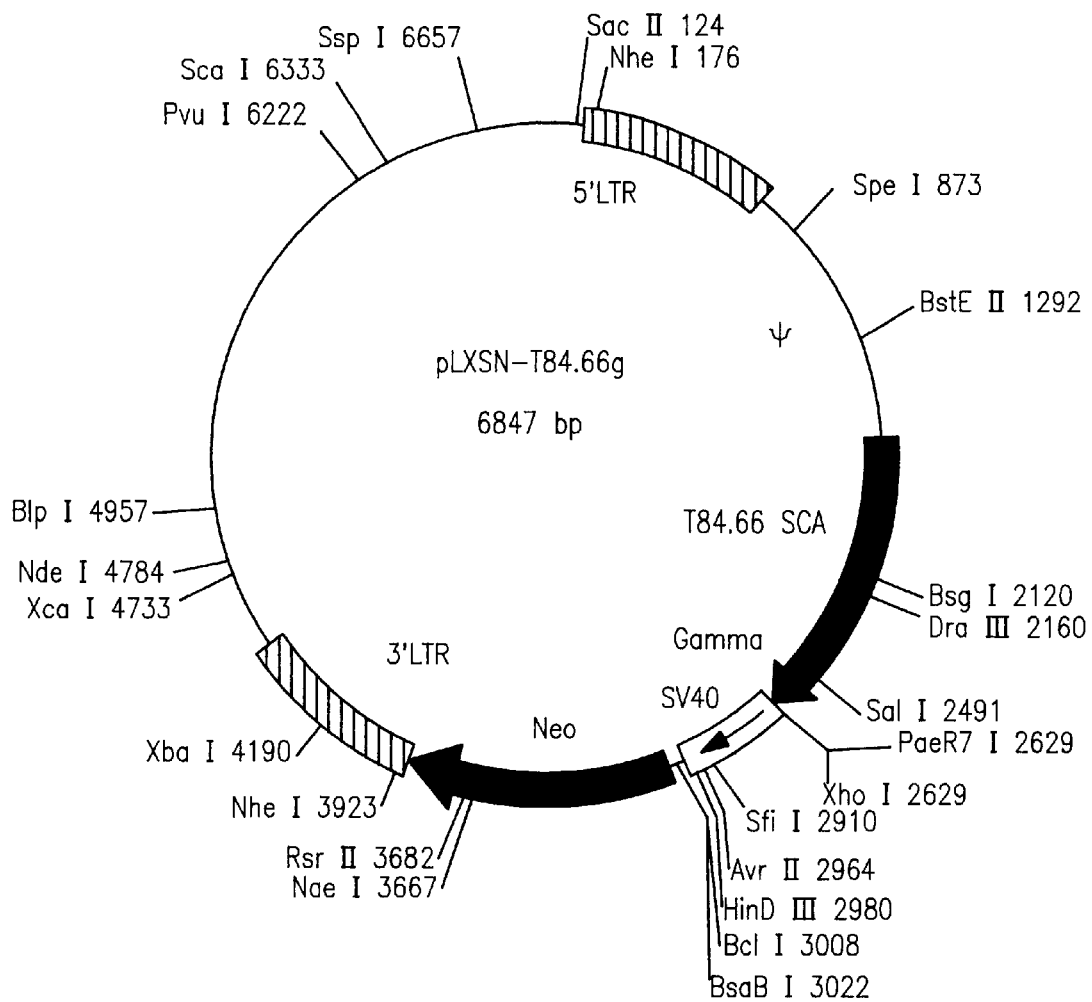
FIG. 2 is a map of the plasmid pLXSN-T84.66g.

The gene transfer vector used in this embodiment of the invention is preferably a retroviral vector, containing a suicide gene and a suitable selectable marker. The retroviruses used in the Examples which follow are the product of the following vectors: 1) pLXSN-T84.66g, 2) pLXSN-N29g, and the Tk retroviral vector which produces the DAHSVTK9A retrovirus (Viagene, San Diego, Calif.). The maps of the first two vectors are provided in FIGS. 1 and 2, respectively. The overall map of the Tk retroviral vector (DAHSVTK9A) is shown in FIG. 3. FIG. 4 depicts the structure of the RVV HSV-TK provector.

The pLXSN-T84.66g and pLXSN-N29g vectors have the neo gene under control of the SV40 promoter, and retroviral 5' LTR, 3' LTR and ψ packaging sequences. The retroviral Tk vector (DAHSVTK9A) has a HSV-tk gene transcribed under control of the Moloney 5' LTR early promoter and a neo gene transcribed under control of the SV40 promoter. The RVV HSV-TK provector also has a HSV-tk gene transcribed under control of the Moloney 5' LTR early promoter and a neo gene transcribed under control of the SV40 promoter.

Thus, in one embodiment, a retroviral gene delivery vector including a suicide gene (e.g., a HSV-tk gene) is prepared as described above, and used to transduce a population of T cells as described above. General T cell transduction methodologies are described in commonly owned U.S. patent application Ser. No. 08/425,180, filed Apr. 30, 1995, now abandoned, entitled "High Efficiency ex vivo Transduction of Cells by High Titer Recombinant Retroviral Preparations," which application is incorporated herein by reference. Other methods of growing and transducing T cells can be used and are known to those skilled in the art (e.g., Chuck et al. (1996) *Hum. Gene Ther.* 7:743; Heslop et al. (1996) *Nature Med.* 2:551; Riddell et al. (1996) *Nature Medicine* 2:216). T cells can also be transduced by methods used to grow and transduce T cells from HIV patients (e.g., Vandenddriessche et al. (1995) *J. Virol.* 69:4045; Sun et al. (1995) *Proc. Natl. Acad. Sci. U.S.A.* 92:7272).

The T cell-transduction method described herein can be used to obtain a transduction efficiency of 100% or greater in a non-selected population of transduced T cells. This transduction efficiency has heretofore not been attainable using prior methodology.

After transduction, transduced cells are selected away from non-transduced cells using known techniques. For example, if the gene transfer vector used in the transduction includes a selectable marker which confers resistance to a cytotoxic agent, the cells can be contacted with the appropriate cytotoxic agent, whereby non-transduced cells can be negatively selected away from the transduced cells. If the selectable marker is a cell surface marker, the cells can be contacted with a binding agent specific for the particular cell surface marker, whereby the transduced cells can be positively selected away from the population. The selection step can also entail fluorescence-activated cell sorting (FACS) techniques, such as where FACS is used to select cells from the population containing a particular surface marker, or the selection step can entail the use of magnetically responsive particles as retrievable supports for target cell capture and/or background removal.

More particularly, positive selection of the transduced cells can be performed using a FACS cell sorter (e.g. a FACSVantage™ Cell Sorter, Becton Dickinson Immunocytometry Systems, San Jose, Calif.) to sort and collect transduced cells expressing a selectable cell surface marker. Following transduction, the cells are stained with fluorescent-labeled antibody molecules directed against the particular cell surface marker. The amount of bound antibody on each cell can be measured by passing droplets containing the cells through the cell sorter. By imparting an electromagnetic charge to droplets containing the stained cells, the transduced cells can be separated from other cells. The positively selected cells are then harvested in sterile collection vessels. These cell sorting procedures are described in detail, for example, in the FACSVantage™ Training Manual, with particular reference to sections 3-11 to 3-28 and 10-1 to 10-17.

Positive selection of the transduced cells can also be performed using magnetic separation of cells based on expression or a particular cell surface marker. IN such separation techniques, cells to be positively selected are first contacted with specific binding agent (e.g., an antibody or reagent the interacts specifically with the cell surface marker). The cells are then contacted with retrievable particles (e.g., magnetically responsive particles) which are coupled with a reagent that binds the specific binding agent (that has bound to the positive cells). The cell-binding agent-particle complex can then be physically separated from non-labelled cells, for example using a magnetic field. When using magnetically responsive particles, the labelled cells can be retained in a container using a magnetic filed while the negative cells are removed. These and similar separation procedures are described, for example, in the Baxter Immunotherapy Isolex training manual.

Expression of the vector in the selected transduced cells can be assessed by a number of assays known to those skilled in the art. For example, Western blot or Northern analysis can be employed depending on the nature of the inserted nucleotide sequence of interest. Once expression has been established and the transformed T cells have been tested for the presence of adventitious agents, they are ready for infusion into a patient via the peripheral blood stream.

The invention further includes a kit for genetic modification of an ex vivo population of primary mammalian cells. The kit contains a gene transfer vector coding for at least one selectable marker and at least one nucleotide sequence of interest contained in one or more containers, ancillary reagents or hardware, and instructions for use of the kit. The instructions can be recorded on any suitable medium such as paper, plastic, magnetic media, or on a CD.

The container or containers can be hermetically sealed so as to physically separate the contents from the environment to prevent the exchange of moisture, gases, particles, microbes, viruses, and the like. Such containers can be glass or plastic vials, ampules, or rubber-stopped containers from which samples can be repeatedly removed using, for example, a syringe. The gene transfer vector therein can be stored in a frozen, liquid, or lyophilized form in a variety of media designed for the storing of such vectors. Storage conditions such as temperature, time, and storage media, will vary depending on the particular vector used, and are readily determined by one of skill in the art. The containers can also include other reagents such as buffers (i.e. PBS), salts (i.e. multivalent ions), and stabilizing and preserving agents (i.e. glycerol and antioxidants). Additional reagents useful for practicing the particular genetic modification method can be included in the vial containing the gene transfer vector or in other vials.

Ancillary reagents and/or hardware can also be contained in the kits. Examples are buffers, reagents, containers, syringes, pipettes, needles, tubing, biocompatible plastic bags, closed fluid pathways, closed culture environments, and the like. All ancillary reagents and hardware necessary to practice a method need not be provided in a single kit.

In one particular embodiment, a production kit is provided. The production kit contains and/or describes all components, elements and processes necessary for ex vivo production of genetically modified primary mammalian cells. The components of the production kit can thus comprise or describe: (1) devices and hardware systems (e.g., cell separation and/or processing equipment for production of transduced cells, for example, a Fenwal® Model CS3000 blood cell separator, a Terumo Sterile Connect Device (Baxter), and the like); (2) a gene within a gene delivery vector (the gene of interest contained within a suitable gene delivery vector, wherein the gene delivery vector is suitably formulated for inclusion within a sterile closed single-use container configured for use with the above-described devices and hardware systems); (3) disposable containers (e.g., disposable single-use containers for manipulation, culture, handling, and/or cryopreservation of the ex vivo modified cells, wherein the containers are sterile, biocompatible, and suitable for use with closed fluid pathway maintenance and configured for use with the above-described devices and hardware systems); (4) reagents and solutions (e.g., any reagents and/or solutions for use in the manipulation, culture, handling or cryopreservation of the ex vivo modified cells, wherein the reagents and solutions can be contained within sterile containers and adapted for use with the above-described devices and hardware systems); (5) biologics (e.g., biological agents and/or reagents for use in the manipulation, culture, handling or cryopreservation of the ex vivo modified cells, including growth factors, mitogens, and cell selection reagents such as antibody molecules or other specific binding agents); (6) ancillary reagents (e.g., those used for selection and/or enrichment of cells expressing selectable markers from a population of genetically modified cells, such as magnetically responsive particles or selection reagents (G418)); and (7) instructions (e.g., protocol describing the manufacturing procedures required to produce genetically modified cells in accordance with the present invention).

Thus, a number of embodiments of the invention have been described. In the Examples below, particular embodiments of the invention are exemplified. In Example 1, high efficiency transduction methods are used to produce $1 \times 10^9$ Tk-Neo®-transduced T cells. This cell number will accommodate both multiple dosing in an ex vivo gene therapy protocol and all appropriate quality control sampling. To date, most clinical studies have been performed in an open culture system using multi-well tissue culture plates. These systems are not acceptable or practical for generating clinical materials because they are susceptible to contamination and are not commercially useful. In the methods of the following examples, automated washing procedures allow for complete medium exchanges whereby ancillary components such as bovine serum are removed from the culture media in volume exchange procedures.

High-dose chemotherapy followed by allogeneic bone marrow transplantation (BMT) for the treatment of multiple myeloma and leukemia has a curative potential attributed to graft vs. host disease (GVHD) and graft vs. leukemia (GVL) effects. However, allogeneic BMT recipients have an unreasonably high incidence of severe and lethal GVHD. To solve this problem, T cell depletion of the BMT has been used. Using this approach, the incidence of GVHD is decreased; However, engraftment success and patient survival has also decreased. Therefore, a preferred strategy in allogeneic BMT would combine a means of effectively controlling GVHD without interfering with GVL or engraftment.

One strategy, then, is to genetically modify donor T cells to express a suicide gene prior to infusion. For example, the methods of the invention can be used to genetically modify T cells to express the Herpes Simplex Virus Thymidine Kinase (HSV-TK) suicide gene. Such genetically modified T cells (expressing HSV-TK) are thus rendered susceptible to ganciclovir (GCV) (Syntex Laboratories, Palo Alto, Calif.), a drug tolerated by unmodified cells but deleterious to cells which express HSV-TK. Because the initial activation of the prodrug is catalyzed by viral thymidine kinase, only the genetically modified cells are affected. These modified donor T cells can then be infused with T cell-depleted bone marrow to provide the beneficial effects of GVL with engraftment. Subsequent GVHD can be controlled by administering GCV to reduce alloreactive T cells.

The generation of up to about $1 \times 10^{11}$ genetically modified T lymphocytes for adoptive cell transfer poses several challenges. Manual large-scale production techniques for generating lymphokine-activated killer cells (LAK) for tumor immunotherapy requires manual separation, washing, and centrifugation. The processing of cells for each patient requires approximately 400 entries into tubes, flasks and roller bottles (Lee et al. (1994) *Transfusion Medicine* 8:1203). The procedures described herein provide several advantages in large-scale production methods by eliminating a majority of the above-described manual techniques in a closed fluid system that maximizes the use of automated fluid separation and/or handling techniques.

After transduction, the T cells may be administered to a suitable vertebrate subject. In addition, although warm-blooded animals (e.g., mammals or vertebrates such as humans, macaques, horses, cows, swine, sheep, dogs, cats, chickens, rats and mice) have been exemplified in the methods described above, such methods are also readily applicable to a variety of other animals, including, for example, fish.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

High Efficiency Transduction of T Cells

This example demonstrates an efficient cell-processing procedure in which T cells are activated, transduced with Tk-Neo® retrovirus, selected in G418, and expanded in a closed system. This procedure readily yields at least $1 \times 10^9$ transduced T cells and demonstrates the feasibility of using this protocol for the transduction of T cells on the scale needed for clinical applications.

In order to evaluate the best media for activation of T cells by OKT-3, the growth kinetics of T cells cultured in 31 different growth media were determined as follows. Briefly, mononuclear cells were isolated from freshly drawn peripheral blood using Ficoll-Hypaque® (Sigma Chemical Co., St. Louis, Mo.) density-gradient separation. Peripheral blood mononuclear cells were seeded in 6-well plates at $0.5 \times 10^6$ cell/ml in each medium or solution containing 60IU/ml rIL-2 (recombinant human IL-2, Chiron, Emeryville, Calif.) and 10 ng/ml OKT-3 antibody (Ortho Biotech, Raritan, N.J.), and cultured at 37° C. in 5% $CO_2$. For each experiment, control mononuclear cells were seeded at $0.5 \times 10^6$ cells/ml in AIM V (GIBCO/BRL Life Technologies, Gaithersberg, Md.) +10% Fetal Bovine Serum (FBS; Biowhittaker, Walkersville, Md.), 60IU/ml rIL-2 and 10 ng/ml OKT-3.

Three days after activation by OKT-3, cells were harvested by centrifugation, counted, and resuspended in the same media or solution without OKT-3 at $0.5 \times 10^6$ cells/ml. Viability was determined by trypan blue exclusion. Cell cycle analysis was performed by FACS analysis before OKT-3-activation and three days after OKT-3-activation. From these data, the percentage of cells in the (S+G2/M) stage of the cell growth cycle was calculated for each of the media tested. AIM V +7% FBS media resulted in the largest percentage of cells in the S+G2/M stage, and was thus selected for further development of transduction and cell processing protocols as set forth below.

Large Scale Cell Processing and Transduction Protocol

T cells were isolated, OKT-3-activated, transduced, G418-selected, and expanded as described below. T cells were obtained from the leukapheresis product of three donors, hereinafter referred to as A05, A06, and A07. For production of the apheresis product, a suitable blood separator (e.g., a CS3000 Blood Cell Separator (Baxter Fenwall) or a Cobe Spectra Hemometrics separator) was used.

Isolation of Mononuclear Cells by Ficoll-Hypaque® Procedure

In order to provide purified human mononuclear cells, the following procedure was carried out. The apheresis product of human donors A05, A06 and A07 was isolated using Open System Apheresis Kits (Baxter Fenwal) according to the manufacturer's instructions. The apheresis product was transferred to Lifecell® Product Flasks containing 200 ml of saline/ACD solution (Baxter Fenwal) and diluted using the Fenwal® CS-3000® Plus Blood Cell Separator (Baxter Fenwal) following the manufacturer's instructions. The apheresis product had at least about $3 \times 10^9$ mononuclear cells. Apheresis products having less than about this number of cells were not taken any farther in the procedure. The characteristics of the cells thus collected are set forth in Table 1.

TABLE 1

CELL PARAMETERS OF APHERESIS PRODUCTS

| Characteristic | Donor A05 | Donor A06 | Donor A07 |
|---|---|---|---|
| Viability (%) | 99 | 99 | 99 |
| Vol. (ml) | 161 | 172 | 172 |
| Cell Density ($\times 10^6$/ml) | 25.4 | 22.4 | 35.7 |
| Total# ($\times 10^9$/ml) | 4.1 | 3.9 | 6.1 |
| % Cells in S + G2/M | 0.2 | 1.1 | 0.3 |
| CD Marker Profile | | | |
| % CD3+ | 72 | 39 | 61 |
| % CD3+ CD4+ | 46 | 23 | 42 |
| % CD3+ CD8+ | 26 | 17 | 21 |
| % CD3− CD16+ | 11 | 26 | 16 |
| % CD3+ CD56+ | 1 | 5 | 6 |
| % CD3− CD56+ | 12 | 25 | 21 |
| % CD3+ CD25+ | 2 | 2 | 8 |
| % CD3+ CD28+ | 67 | 3.0 | 51 |
| % CD3+ HLA-DR+ | 2 | 2 | 2 |
| % CD3− HLA-DR+ | 14 | 35 | 16 |

Mononuclear cells were isolated from diluted apheresis product using the Fenwal® CS-3000® Plus by Ficoll- Hypaque® density centrifugation following the manufacturer's instructions. The Ficoll®-Hypaque purification procedure yielded about $2 \times 10^9$ to about $5 \times 10^9$ mononuclear cells. The purified cellular product must have approximately $1 \times 10^9$ mononuclear cells in order to be used in the later procedures. A portion of the mononuclear cells ($3 \times 10^8$) was reserved for OKT-3 activation. Excess cells were cryopreserved in Cryocyte® containers (Baxter Fenwal). The yield and viability of the Ficoll®-Hypaque® purified cells were determined; the results are shown in Table 2.

The Ficoll®-Hypaque® purified mononuclear cell product was transferred using sterile technique from the CS-3000® Plus Harvest Chamber to a tared Fenwal® Transfer Pack Flask. Collection of quality control samples from closed system Lifecell® Flasks was performed using a Fenwal® Plasma Transfer Set (Baxter Fenwal). The contents of the Lifecell® Flask were mixed to attain an even cell suspension before a portion of the culture was drained from the Lifecell® Flask into a sterile sample tube.

Cells were frozen in aliquots of no more than $50 \times 10^6$ cells/ml in Cryocyte® containers with ⅓ cell volume of 3× Freezing Solution (10% AIM V media, 60% FBS, and 30% DMSO). If desired, the freezing solution can employ 20% autologous plasma in order to avoid bovine products (FBS). Frozen cell samples were stored in liquid nitrogen.

TABLE 2

CHARACTERISTICS OF FICOLL ® PURIFIED WHITE BLOOD CELLS

| Characteristic | DONOR A05 | DONOR A06 | DONOR A07 |
|---|---|---|---|
| Viability (%) | 95 | 93 | 96 |
| Vol. (ml) | 188 | 197 | 185 |
| Cell Density ($\times 10^6$/ml) | 9.9 | 13.7 | 18.3 |
| Total ($\times 10^9$/ml) | 1.9 | 2.7 | 3.4 |
| Recovery (%) | 46 | 69 | 55 |

OKT-3 Activation of the T-Cells

In order to ensure that the cells were optimally receptive to infection by retrovirus, the following activation procedure was carried out. At least about $3 \times 10^8$ Ficoll-Hypaque®-purified mononuclear cells were distributed equally into 1L Lifecell® Flasks in Lymphocyte Activation Media (AIM V with 10% FBS, 2 mM glutamine, 60IU/ml rIL-2 and 10 ng/ml OKT-3) to achieve a final cell concentration of $5 \times 10^5$ mononuclear cells/ml in about 200 to about 400 mL of media. Ficoll®-purified mononuclear cell product first was manually distributed into empty Lifecell® Flasks using Sepacell® Adapter Sets and a Plasma Transfer Set, and a 60 cc syringe, followed by the Activation Media.

The Lifecell® Flasks containing the Ficoll®-purified cells in Lymphocyte Activation Media were incubated on wire racks at about 37° C. at about 5% $CO_2$ for approximately three days. Wire racks were used to enhance gas exchange. The results of the OKT-3-activation procedures described above are summarized in Table 3.

TABLE 3

| | OKT-3-ACTIVATION | | |
|---|---|---|---|
| OKT-3 Acitivation | DONOR A05 | DONOR A06 | DONOR A07 |
| # cells set up ($\times 10^8$) | 3 | 3 | 3 |
| Viability | 95 | 93 | 96 |

TABLE 3-continued

| | OKT-3-ACTIVATION | | |
|---|---|---|---|
| OKT-3 Acitivation | DONOR A05 | DONOR A06 | DONOR A07 |
| # cells/ml set up ($\times 10^6$) | 0.5 | 0.5 | 0.5 |
| Total Volume (ml) | 600 | 600 | 600 |
| CD Marker Profile | | | |
| % CD3+ | 47 | 24 | 53 |
| % CD3+ CD4+ | 33 | 15 | 38 |
| % CD3+ CD8+ | 14 | 10 | 16 |
| % CD3− CD16+ | 18 | 37 | 2 |
| % CD3+ CD56+ | 0 | 3 | 6 |
| % CD3− CD56+ | 21 | 35 | 23 |
| % CD3+ CD25+ | 1 | 2 | 5 |
| % CD3+ CD28+ | 43 | 17 | 40 |
| % CD3+ HLA-DR+ | 2 | 2 | 2 |
| % CD3− HLA-DR+ | 36 | 38 | 24 |

Harvesting of T-cells Prior to Retroviral Transduction

About three days after OKT-3 activation, the activated mononuclear cells were harvested from the Lymphocyte Activation Media using the single chamber method of the CS-3000® Plus essentially as set forth in the manufacturer's instructions. Samples of the OKT-3-activated cells were taken aseptically for quality control testing using the Tube Stripper (Baxter Fenwal) to obtain a small length of tubing containing the aliquot to be tested. The harvested activated mononuclear cells were transferred to tared 1L Lifecell® Flasks, retaining 20 ml samples for quality control testing.

The characteristics of the harvested activated mononuclear cells are set forth below in Table 4. As shown in Table 4, the activation procedure yielded greater than about $1 \times 10^8$ mononuclear cells. The glucose concentration of the culture was greater than about 100 mg/dL, and the lactate concentration was less than about 1.0 mg/ml. These parameters are the threshold release criteria for the methods which follow.

In preparation for transduction, at least about $1.5 \times 10^8$ harvested, OKT-3-activated mononuclear cells in Lymphocyte Transduction Media (AIM V with 10% FBS, 2 mM glutamine, 60IU/rIL-2, and 5 µg/ml Protamine sulfate) were delivered manually into 1L Lifecell® Flasks at a concentration of about $5 \times 10^5$ mononuclear cells/ml. The preferred total volume of the combined harvested, activated mononuclear cells and Lymphocyte Transduction Media was about 200 to about 400 ml per 1 Liter Lifecell® Flask, with a maximum volume of about 500 ml. Small samples (5 ml each) of the combined harvested, activated mononuclear cells and the Lymphocyte Transduction Media were frozen for later sterility testing at a later time. The concentration of glucose and lactate in the samples was determined using a YSI-2700 Glucose Analyzer (Yellow Springs Instrument Co., Yellow Springs, Ohio) following the manufacturer's instructions.

TABLE 4

CHARACTERISTICS OF HARVESTED ACTIVATED MONONUCLEAR CELLS

|  | DONOR A05 Single Chamber on CS-3000 ® | DONOR A06 Single Chamber on CS-3000 ® | DONOR A07 Single Chamber on CS-3000 ® |
|---|---|---|---|
| Pre-Harvest Cell # ($\times 10^8$) | 6.2 | 6.6 | 6.9 |
| Viability (%) | 95 | 100 | 96 |
| # cells/ml ($\times 10^6$) | 1.0 | 1.1 | 1.2 |
| Post-Harvest Cell # ($\times 10^8$) | 5 | 4.3 | 5.1 |
| Viability (%) | 90 | 97 | 97 |
| % Recovery | 81 | 65 | 74 |
| Lactate (g/L) | 0.918 | 0.683 | 0.683 |
| Glucose (g/L) | 1.88 | 2.15 | 2.1 |
| % Cells in S + G2/M | 57.8 | 55.5 | 62.5 |
| CD Marker Profile |  |  |  |
| % CD3+ | 82 | 82 | 84 |
| % CD3+ CD4+ | 62 | 57 | 64 |
| % CD3+ CD8+ | 21 | 25 | 20 |
| % CD3− CD16+ | 2 | 5 | 2 |
| % CD3+ CD56+ | 1 | 2 | 3 |
| % CD3− CD56+ | 3 | 6 | 3 |
| % CD3+ CD25+ | 96 | 82 | 90 |
| % CD3+ CD28+ | 93 | 76 | 80 |
| % CD3+ HLA-DR+ | 41 | 57 | 41 |
| % CD3− HLA-DR+ | 10 | 10 | 8 |

Retroviral Transduction of T-Cells

Moloney Murine Leukemia Virus (MMLV)-derived retroviral supernatant (DAHSVTK9A) ($3.9 \times 10^7$ CFU/ml; Viagene Corp., San Diego, Calif.) was purchased from the manufacturer. The supernatant preparation was added to the OKT-3-activated mononuclear cells at a multiplicity of infection (MOI) of at least about 3:1 to greater than about 5:1 according to the procedures set forth below.

The retroviral supernatant preparation was stored at −70° C. Just prior to use, the supernatant preparation was thawed aseptically in a 37° C. water bath with gentle agitation. The retroviral material was injected immediately into the Lifecell® Flask, ensuring fluid-to-fluid contact. A new syringe and needle were used for each Lifecell® Flask.

Supernatant preparations with a titer of less than $1.5 \times 10^7$ cfu/ml were added directly to the Lymphocyte Transduction Media. In cases where the titer of the supernatant was less than about $1.5 \times 10^6$, the retroviral material was applied directly to the cells without further dilution with AIM V medium. In this situation, the Protamine sulfate and rIL-2 were added directly into the retroviral supernatant without the addition of AIM V, L-Glutamine, or FBS. Supernatant preparations with a titer of greater than about $1.5 \times 10^7$ cfu/ml were delivered to Lifecell® Flasks containing cells and Transduction Media.

A sample of the supernatant preparation was reserved for immediate titration using the murine cell line NIH3T3, the human cell lines HT1080 and 143B, and the canine cell line Cf2Th. The particular indicator cell line used to assay a supernatant preparation depends upon the host range of the viral vector being analyzed. Titers were determined using the general method of Cepko, *Current Protocols in Molecular Biology,* Greene Pub. Associates and Wiley-Interscience, New York (1992), which is herein incorporated by reference, except that the titer was determined by counting the number of cells per plate on the first and second day of the assay to more accurately determine the titer.

TABLE 5

PARAMETERS FOR CELLS TO BE TRANSDUCED

| Transduction | DONOR A05 | DONOR A06 | DONOR A07 |
|---|---|---|---|
| # Cells Transduced ($\times 10^8$) | 1.5 | 1.5 | 1.5 |
| # Cells/ml set up ($\times 10^6$) | 0.5 | 0.5 | 0.5 |

Optional Post-Transduction Cell Expansion #1

Transduced mononuclear cells can be optionally expanded following transduction. The purpose of such an expansion is to ensure that a sufficient number of transduced cells are present in the culture and thus survive G418 selection. The G418 selection step described below was performed without expansion if the total cell number in the initial activated, transduced culture was greater than about $3 \times 10^8$ cells. For cell numbers less than about $3 \times 10^8$, the following post-transduction expansion procedures should be followed.

During expansion, the cell count, viability, and glucose and lactate concentrations were measured about every two days. The glucose concentration in the culture should be greater than about 100 mg/dL and the lactate concentration in the culture should be less than about 1.0 mg/ml for the sample to be used in later procedures.

White blood cell counts were determined using a Sysmex® K-1000 cell counter (TOA Medical Electronics, Kobe, Japan) following the manufacturer's instructions, paying particular attention to the following modifications. When the cell count became greater than $99.9 \times 10^6$/ml, samples were diluted 1:10 with D-PBS.

Lymphocyte Culture Media was prepared by adding nutritional and growth supplements to the AIM V Media to produce final concentrations of 10% FBS, 2 mM Glutamine and 60 IU/ml rIL-2. Glucose and lactate concentrations were determined as described above, and the media was used the same day it was prepared.

For a cell density of at least $2 \times 10^6$ cells/ml, transduced mononuclear cells were expanded by diluting them to about $5 \times 10^8$ cells/ml in Lymphocyte Culture Media in Lifecell® Flasks. Samples which had less than about $5 \times 10^8$ total white blood cells were dispensed at about $5 \times 10^5$ cells/ml into 1L Lifecell® Flasks. Samples which had greater than about $5 \times 10^8$ total white blood cells were dispensed at about $5 \times 10^5$ cells/ml into 3L Lifecell® Flasks. Cultures were incubated at 37° C./5% $CO_2$ as described above. The results of the first expansion of A05, A06 and A07 donor cells are set forth in Table 6.

TABLE 6

POST-TRANSDUCTION EXPANSION #1

| Post-Transduction Expansion 1 | DONOR A05 | DONOR A06 | DONOR A07 |
|---|---|---|---|
| Cell # ($\times 10^8$) | 4.2 | 3.9 | 3.9 |
| # cells/ml ($\times 10^6$) | 1.4 | 1.3 | 1.3 |

TABLE 6-continued

POST-TRANSDUCTION EXPANSION #1

| Post-Transduction Expansion 1 | DONOR A05 | DONOR A06 | DONOR A07 |
|---|---|---|---|
| Viability (%) | 90 | 94 | 93 |
| Reseeded at # cells/ml ($10^6$) | 0.5 | 0.5 | 0.5 |
| Total Volume (ml) | 840 | 780 | 780 |

Optional Post-Transduction Cell Expansion #2

For total cell numbers at the end of the first post-transduction expansion step equal to or greater than $3 \times 10^8$ cells, the second post-transduction expansion step was omitted. When cell density became greater than about $2 \times 10^6$ cells/ml, transduced mononuclear cells were expanded by diluting them to about $5 \times 10^5$ white blood cells/ml in Lymphocyte Culture Media in 1L Lifecell® Flasks. For expansion cultures which had a total number of less than about $5 \times 10^8$ white blood cells, cells were dispensed and diluted at a concentration of about $5 \times 10^5$ cells/ml into 1L Lifecell® Flasks. Expanded cultures having a total number of greater than about $5 \times 10^8$ white blood cells were dispensed and diluted at a concentration of about $5 \times 10^5$ cells/ml into 3L Lifecell® Flasks.

Expanded cultures were incubated at 37° C. with 5% $CO_2$ as described above. Cell number, viability, and glucose and lactate concentrations of activated, transduced mononuclear cell cultures were determined as described above about every two days after the first post-transduction expansion. The results obtained in the second expansion are set forth in Table 7.

TABLE 7

POST-TRANSDUCTION EXPANSION #2

| Post-Transduction Expansion 2 | DONOR A05 | DONOR A06 | DONOR A07 |
|---|---|---|---|
| Cell # ($\times 10^9$) | 1.8 | 1.6 | 1.5 |
| # cells/ml ($\times 10^6$) | 2.2 | 2.1 | 2 |
| Viability (%) | 92 | 94 | 88 |
| Lactate (g/L) | 0.911 | 0.993 | 0.826 |
| Glucose (g/L) | 1.86 | 1.72 | 1.89 |
| Reseeded at # cells/ml ($\times 10^6$) | 0.5 | 0.5 | 0.5 |
| Total Volume (ml) | 3600 | 3200 | 3000 |

Harvesting of Expanded Cells

Cells were harvested when the total number of expanded cells became greater than about $3 \times 10^9$ cells. The transduced mononuclear cells from donor A05 were harvested using the single chamber method of the CS-3000® Plus following the manufacturer's instructions as discussed above. The transduced cells from donors A06 and A07 were harvested using a Autopheresis C with a 2 µm filter at 1200 rpm. Characteristics of the cells harvested prior to G418 selection are set forth below in Table 8.

TABLE 8

CHARACTERISTICS OF HARVESTED CELLS EXPANDED FOR G418 SELECTION

| Method of Harvest | DONOR A05 Single chamber on CS-3000® | DONOR A06 Auto-pheresis C | DONOR 07 Auto-pheresis C |
|---|---|---|---|
| Pre-Harvest Cell # ($\times 10^9$) | 2.9 | 2.6 | 2.6 |
| Viability (%) | 96 | 96 | 98 |
| # cells/ml | 0.8 | 0.8 | 0.9 |
| Post-Harvest Cell # ($\times 10^9$) | 2.3 | 1.5 | 2 |
| Viability (%) | 98 | 97 | 98 |
| % Recovery | 79 | 58 | 78 |
| Lactate (g/L) | 0.368 | 0.418 | 0.41 |
| Glucose (g/L) | 2.63 | 2.51 | 2.51 |
| CD Marker Profile | | | |
| % CD3+ | 97 | 99 | 99 |
| % CD3+ CD4+ | 54 | 51 | 45 |
| % CD3+ CD8+ | 45 | 50 | 56 |
| % CD3− CD16+ | 0.0000 | 0.0800 | 0.0000 |
| % CD3+ CD56+ | 1 | 1 | 3 |
| % CD3− CD56+ | 0.0000 | 0.0000 | 0.0000 |
| % CD3+ CD25+ | 36 | 93 | 78 |
| % CD3+ CD28+ | 98 | 89 | 78 |
| % CD3+ HLA-DR+ | 61 | 71 | 69 |
| % CD3− HLA-DR+ | 1 | 1 | 2 |

G418 Selection

Harvested transduced mononuclear cells were diluted and dispensed at a concentration of about $5 \times 10^5$ cells/ml in G418 Selection Media using manual distribution methods. Harvested populations having less than about $5 \times 10^8$ total white blood cells were diluted and dispensed at a concentration of about $5 \times 10^5$ cells/ml into 1L Lifecell® Flasks. Harvested populations having greater than about $5 \times 10^8$ white blood cells were diluted and dispensed at a concentration of about $5 \times 10^5$ cells/ml into 3L Lifecell® Flasks.

G418 Selection Media (10% FBS, 2 mM Glutamine, 0.8 mg/ml G418 and 60 IU/ml rIL-2 in AIM V media) was prepared using heat-inactivated FBS, 100× L-Glutamine, and rIL-2. G418 was added at a concentration of 0.8 mg/ml active drug. G418 is commercially available as a powder and is very stable. However, because the potency of G418 varies considerably from lot to lot, and is generally low (about 450 µg/mg of powder), care must be taken to note the specific activity of each lot and to apply the drug at appropriate concentrations. As for other media, glucose and lactate concentrations were determined, and the selection media was used the same day it was prepared.

A small sample (5 ml) of the G418 Selection Media was reserved for quality control testing using the closed-system transfer methods discussed above. The cultures were incubated at 37° C. with 5% $CO_2$. The results obtained from this procedure are set forth in Table 9.

TABLE 9

G418 SELECTION

| Initiate G418 Selection | DONOR A05 | DONOR A06 | DONOR A07 |
|---|---|---|---|
| # Cells set up in G418 Selection ($\times 10^9$) | 1.8 | 1.4 | 1.9 |

TABLE 9-continued

G418 SELECTION

| Initiate G418 Selection | DONOR A05 | DONOR A06 | DONOR A07 |
|---|---|---|---|
| # cells/ml set up ($\times 10^6$) | 0.5 | 0.5 | 0.5 |
| Total Volume (ml) | 3600 | 2800 | 3800 |
| Viability (%) | 98 | 97 | 98 |
| Monitor Cells (At 2 Days) | | | |
| Total Cell # ($\times 10^9$) | 2.0 | 1.7 | 3.8 |
| # cells/ml ($\times 10^6$) | 9.7 | 0.6 | 1 |
| Viability | 94 | 91 | 95 |

Optional Feeding with Fresh Selection Media

If desired, the mononuclear cells are fed with fresh G418 Selection Media, prepared as discussed above, after about two days. Cell density is maintained at about $5\times10^5$ cells/ml. Samples of the cell cultures can be taken prior to harvesting for quality control testing.

Cells are harvested using a Fenwal® Plasma Extractor following the manufacturer's instructions by centrifuging 600 ml Transfer Pack Containers. To ensure proper cell pellet formation, the Transfer Pack Container is filled to 600 ml. The cells are harvested by centrifugation at 1200 rpm (300 g) for 15 minutes. The Transfer Pack Container is gently removed from the centrifuge holder, and the pellet is checked for the formation of a pellet. If no firm pellet has been formed, the Transfer Pack Container is centrifuged for an additional 10 minutes. The Fenwal® Plasma Extractor is used to remove the supernatant.

The transduced and G418-selected mononuclear cells are dispensed at concentrations of about $5\times10^5$ cells/ml into fresh G418 Selection Media. For samples with less than about $5\times10^8$ white blood cells, mononuclear cells are dispensed at a concentration of about $5\times10^5$ cells/ml into 1L Lifecell® Flask for a total final volume of about 200 to 400 ml. Samples having greater than about $5\times10^8$ mononuclear cells are dispensed at a concentration of about $5\times10^5$ cells/ml into 3L Lifecell® Flasks for a total final volume of preferably around one, but no more than about 1.5 liters. Cultures are incubated at 37° C. with 5% $CO_2$.

Optional Neo Selection Expansion #1

Cell count, viability, glucose and lactate concentrations are determined on about the second day of G418 selection, using the Sysmex® K-1000 and the YSI Model 2700 as discussed above. If the cell density exceeds about $2\times10^6$ cells/ml on the second day following G418 selection, transduced mononuclear cells are expanded by diluting them to about $5\times10^5$ cells/ml in G418 Selection Media, prepared as discussed above. If the cell density is less than about $2\times10^6$ cells/ml, culturing is continued and the cell density monitored on the third day after G418 selection.

Samples with less than about $5\times10^8$ total white blood cells are dispensed at about $5\times10^5$ cells/ml into 1L Lifecell® Flasks. Samples with greater than about $5\times10^8$ total white blood cells are dispensed at about $5\times10^5$ cells/ml into 3L Lifecell® Flasks. Cultures are incubated at 37° C. with 5% $CO_2$.

Harvesting

About four days following the initiation of G418 selection, G418 selection media was removed from the cell culture by gently harvesting the selected mononuclear cells using one of the following Options 1, 2, or 3.

Harvesting by Centrifugation

G418 Selection Media was removed using the Fenwal® Plasma Extractor following the manufacturer's instructions as discussed above.

Harvesting by Ficoll®-Hypaque

For cultures having a viability of greater than 50%, G418 Selection Media and dead cells were removed with the CS-3000® Plus using Ficoll-Hypaque® separation procedures according to the manufacturer's instructions.

A 1000 ml Lifecell® Flask containing AIM V Media and fitted with a Plasma Transfer Set with Spike and Needle Adapter was connected to the Saline and Vent lines using the Sterile Tubing Welder (one lead to the vent and another lead to the saline line). A 600 ml Transfer Pack Container (for product) and a 2000 ml Transfer Pack Container (for waste) were aseptically docked to the Plasma Collect line using the "Y" tubing leads obtained from an 800 ml Transfer Pack Unit with two couplers. The roller clamps on the Saline, Vent, and Plasma Collect lines were then opened. The Inlet, Return, and ACD line roller clamps were closed.

Receipt of the apheresis product was performed using the following procedure. When spiking Flasks using spike couplers, it is important to ensure that spikes are securely inserted, as improper insertion may result in the formation of air blocks. The cells were gently resuspended using the sterile tubing welder and transferred to a new 600 ml Transfer Pack Container holding 200 ml of medium. An appropriate amount of saline/ACD from the original Flask was reserved to determine cell count, viability, and sterility. Cell counts were performed using the Sysmex® K-1000 as discussed above. Percent viability of the cells was also determined. The Product/Saline Flask was connected to one lead of a Three Lead-Type Blood Solution Recipient Set. The second lead was attached to a 500 ml Flask of saline ACD. Lastly, the third lead was spiked into one of the two female ports of a Sepacell® Lab Adapter Set. The other female port a Plasma Transfer Set was fitted with a needle adapter, and the needle adapter was inserted into the Ficoll® Flask and the connection secured with adhesive tape. The spiked end of the Sepacell Lab Adapter Set was then heat sealed. A "Y" tubing lead obtained from an 800 ml Transfer Pack Unit was welded to the long lead (retain roller clamp) of the 3 Lead Type Blood-Solution Recipient Set containing the Flasks. The "Y" tubing lead was spliced into line 5 (component rich plasma line) of the Apheresis Set using the Sterile Tubing Welder. The Ficoll® separation procedure was performed essentially according to the manufacturer's instructions.

Harvesting by Autopheresis C

G418 Selection Media was removed using the Autopheresis C following the manufacturer's instructions as described above. The results of harvesting the G418-harvested using the above-described three options are set forth below in Table 10.

TABLE 10

G418-SELECTED CELLS

| Method of Harvest | Centrifugation Extraction | Autopheresis C | Autopheresis C |
|---|---|---|---|
| Pre-Harvest Cell # ($\times 10^9$) | 3.5 | 1.9 | 6.1 |
| Viability (%) | 88 | 74 | 95 |
| # cells/ml ($\times 10^6$) | 1 | 0.7 | 1.6 |
| Post-Harvest Cell # ($\times 10^9$) | 3.2 | 2.9 | 7.5 |
| Viability (%) | 90 | 88 | 96 |
| % Recovery | 91 | 153 | 123 |
| Lactate (g/L) | 0.363 | 0.362 | 0.66 |
| Glucose (g/L) | 2.45 | 2.43 | 2.1 |
| CD Marker Profile | | | |
| % CD3+ | 99 | 100 | 100 |
| % CD3+ CD4+ | 45 | 43 | 44 |
| % CD3+ CD8+ | 57 | 59 | 56 |
| % CD3− CD16+ | 0 | 0 | 0 |
| % CD3+ CD56+ | 1 | 1 | 9 |
| % CD3− CD56+ | 0 | 0 | 0 |
| % CD3+ CD25+ | 16 | 62 | 54 |
| % CD3+ CD28+ | 95 | 82 | 75 |
| % CD3+ HLA-DR+ | 5.0 | 52 | 57 |
| % CD3− HLA-DR+ | 1 | 0 | 1 |

Isolated, transduced, G418-selected mononuclear cells were resuspended at a concentration of about $1\times10^6$ cells/ml in Lymphocyte Culture Media in new Lifecell® Flasks using Flask-to-Flask transfer methods, reserving samples for quality control testing. Another small sample (6 ml) was retained from the culture media using the closed-system distribution methods for Sysmex® K-1000 analysis, cell viability, sterility testing, and Southern Analysis to determine transgene integration.

Cultures having less than about $5\times10^8$ mononuclear cells were dispensed at about $1\times10^6$ cells/ml into 1L Lifecell® Flasks and were incubated at 37° C. with 5% $CO_2$.

Post-Selection Expansion

Post-selection expansion was performed as follows. When the concentration of cells in the culture reached at least about $2\times10^6$ cells/ml, the transduced mononuclear cells were expanded by diluting them to a concentration of about $1\times10^6$ cells/ml in Lymphocyte Culture Media, prepared as described above, into Lifecell® Flasks. Cultures having less than about $5\times10^8$ mononuclear cells were dispensed at about $1\times10^6$ cells/ml into 1L Lifecell® Flasks while cultures having greater than about $5\times10^8$ mononuclear cells were diluted and dispensed at about $1\times10^6$ cells/ml into 3L Lifecell® Flasks. For cell concentrations less than about $2\times10^6$ cells/ml, no expansion was performed. Cell count, viability, and glucose and lactate concentrations were determined at least every two days.

Cryopreservation of Cells and Thawing Cells

About three days after expanding the G418-selected white blood cells, mononuclear cells were harvested using 1 of the 3 harvesting options as described above. Before the cells were harvested, a 35 ml sample of culture media was removed for cell count testing on Sysmex® K-1000; viability testing; analysis of glucose and lactate concentrations with the YSI Model 2700 instrument; cryopreservation; and Southern Blot analysis. A portion of the final harvested cell product and culture medium was retained for quality control testing.

Harvested cells were cryopreserved at a concentration of up to $50\times10^6$ cells/ml in 10% DMSO with 20% human AB serum or autologous plasma in Cryocyte® containers. The cells were frozen in a Control Rate Freezer with a 4° C. starting temperature that dropped at a rate of −1° C./minute to −60° C. and then at a rate of −10° C./minute to −90° C. Samples were stored in the vapor phase of liquid $N_2$.

Determination of HSV-TK Gene Copy Number in Transduced T-Cells

Quantitative Southern Blotting was used to determine the gene copy number per cellular genome in the transduced clinical and analytical scale cell populations using the procedure described below. The variance between assay I and II reveals significant variation in the gene copy number prior to and immediately following G418 selection. For example, three days after G418 was removed, gene copy number increased by two- to ten-fold, indicating that the selection conditions enriched for HSV-TK transduced cells. In assays I and II, transduction efficiencies for cells transduced and grown on a clinical scale displayed a comparable gene copy number of between 0.5 and 1 (see Table 11).

DNA was prepared and analyzed by Southern blotting as follows. Briefly, genomic DNA mini-preps were performed using a Qiagen Kit (Quiagen, Inc., Chatsworth, Calif.) according to the manufacturer's instructions. Genomic DNA was solubilized in pH 8.0 at 65° C. and quantified using a TKO100 device (Hoefer Scientific Instruments, San Francisco, Calif.) according to the manufacturer's instructions.

TABLE 11

SUMMARY OF QUANTITATIVE SOUTHERN BLOT RESULTS FOR CLINICAL SCALE TRANSDUCTION

| | IDENTIFICATION | | | | COPY NUMBER | |
|---|---|---|---|---|---|---|
| Sample Number | Apheresis Number | Plate/ Flask | Code | Day | Assay I | Assay II |
| 1 | A05 | Flask | PACT | 4 | 0.08* | 0.00 |
| 2 | " | " | PTE | 8 | 0.31 | 0.06 |
| 3 | " | " | SE | 12 | ND | 0.10 |
| 4 | " | " | FP | 15 | 0.59 | 0.48 |
| 5 | A05 | Plate | PTE | 4 | 0.48 | 0.19 |
| 6 | " | " | FP | 11 | 0.46 | 0.20 |
| 7 | A06 | Flask | PACT | 4 | ND | 0.00 |
| 8 | " | " | PTE | 8 | 0.09 | 0.13 |
| 9 | " | " | SE | 12 | ND | 0.10 |
| 10 | " | " | FP | 15 | 1.01 | 0.83 |
| 11 | A06 | Plate | PTE | 4 | ND | 0.10 |
| 12 | " | " | FP | 11 | 0.70 | 0.13 |
| 13 | A07 | Flask | PACT | 4 | 0.00 | 0.00 |
| 14 | " | " | PTE | 8 | ND | 0.26 |
| 15 | " | " | SE | 12 | 0.59 | 0.24 |
| 16 | " | " | FP | 15 | 0.52 | 0.66 |
| 17 | A07 | Plate | PTE | 4 | 0.95 | 0.37 |
| 18 | " | " | FP | 11 | 1.02 | 0.47 |

* = No band was visible on the gel
ND = Not determined due to insufficient DNA yield or sample degradation
PACT = Post-OKT-3 Activation Step
PTE = Post Transduction Expansion Step
SE = Selected Cells, day of G418 removal
FP = Final Product, 3 days post-G418 removal Copy number standards were prepared based on a standard of 5 mg of genomic peripheral blood lymphocyte (PBL) DNA per lane. These standards were prepared fresh in siliconized microfuge tubes. The standard stock solution contained 20 ng/ml of pLTIN/Nhe I (7068 bp plasmid/~4 kb fragment). One microliter of each copy number dilution was added to 5 μg of Nhe I-digested huPBL DNA. Preparation of the copy number standards is summarized below in Table 12.

TABLE 12

| SAMPLE | DILUENT (TE) | CONCENTRATION | COPY NO. |
|---|---|---|---|
| 1.18 ml of 20 ng/ml | 48.82 μl | 471.2 pg/ml | 80 |
| 2.5 ml of 471.2 pg/ml | 47.5 μl | 23.56 pg/μl | 4 |
| 20 ml of 23.56 pg/μl | 20 ml | 11.78 pg/ml | 2 |
| 20 ml of 11.78 pg/ml | 20 ml | 5.89 pg/ml | 1 |
| 20 ml of 5.89 pg/ml | 20 ml | 2.95 pg/ml | 0.5 |
| 20 ml of 2.95 pg/ml | 20 ml | 1.47 pg/ml | 0.25 |
| 20 ml of 1.47 pg/ml | 20 ml | 0.736 pg/ml | 0.125 |
| 20 ml of 0.736 pg/ml | 20 ml | 0.368 pg/ml | 0.0625 |

Agarose electrophoresis in Tris-acetate buffer was used to separate the components of these samples according to the general method of Sambrook et al., *Molecular Cloning: A Laboratory Manual,* 2d ed., Cold Spring Harbor Laboratory Press (1989).

Southern blotting was performed on the electrophoresed samples as described below. The DNA in the agarose gel was de-purinated by incubating the gel in 0.25 N HCl for 20 minutes under gentle agitation. The DNA in the agarose gel was denatured by incubating in 0.5 N NaOH–1.5 M NaCl for 20 minutes under gentle agitation. The gel was neutralized by shaking gently in 1 M Tris-HCl pH 7.5–1.5 M NaCl for 20 minutes and the gel was equilibrated by shaking gently in 20×SSC for 20 minutes.

DNA was transferred to a membrane by Southern blotting essentially as described in Reed et al. (1985) *Nuc. Acids Res.* 13(20):7207–7221, which is incorporated herein by reference. The moist membrane was crosslinked in a Stratalinker® (Stratagene, La Jolla, Calif.) and air dried before hybridization.

The blot was pre-hybridized in 10 mg/ml denatured salmon sperm DNA in QuikHyb (Stratagene, La Jolla, Calif.). $^{32}$P-labeled probes were prepared using a Prime-It kit (Stratagene, La Jolla, Calif.) and hybridized in roller bottles or in a hybridization oven. Membranes were washed in 2×SSC/0.1% SDS at room temperature followed by washing five times with 0.1×SSC/0.1% SDS at 65° C. for 30 minutes in a hybridization oven. Autoradiography was performed with an intensifying screen at −70° C. The autoradiographic signals were quantitated using densitometry.

EXAMPLE 2

Clinical Scale Retroviral Transduction

This example demonstrates that about $2\times10^9$ to $2\times10^{11}$ transduced cells can be produced in a closed system. Based on animal tumor models with adoptively transferred Lymphokine Activated Killer (LAK) cells, it is estimated that approximately $1\times10^{11}$ cells are required to treat human tumors (Rosenberg et al. (1990) *New England Journal of Medicine* 323:570). The scale-up procedures described in the present Example generate about $2\times10^{11}$ retrovirally-transduced T-cells in a closed system. As with Example 1, all Fenwal® products are available from Fenwal Division, Baxter Healthcare, Deerfield, Ill.

This procedure follows the procedure set forth in Example 1, unless the instant Example calls for a different or modified procedure.

Isolation of Mononuclear Cells by Ficoll-Hypaque® Procedure

At least $4\times10^9$ white blood cells are obtained from an apheresis product and subject to Ficoll-Hypaque® purification as described in Example 1. Purified product thus obtained is not used if it contains fewer than $2\times10^9$ white blood cells.

OKT-3 Activation of T Lymphocytes

OKT-3 activation of T-cells is carried out substantially as in Example 1. Due to the increased volume, three-liter Lifecell® Flasks were substituted for one-liter Lifecell® Flasks. In addition, cells and medium are transferred among Lifecell® Flasks and the various instruments described below using a Baxter-Fenwal® Solution Transfer Pump (Fenwal® #6455) according to the manufacturer's directions. Lymphocyte Activation Media is prepared as follows using a 10 L AIM V media flask. A Lifecell® Transfer Set (Fenwal® #4C2474) is installed on the Solution Transfer Pump according to the package instructions, as is a Lifecell® Filter Adapter Set (Fenwal® #4C2475). A Sepacell® Laboratory Adapter Set (Fenwal® #4C2459) is inserted into the ten-liter media Flask (adapter sets are then piggybacked, if necessary, to provide additional female ports). A Plasma Transfer Set (Fenwal® #4C2243) is inserted into one of the female ports of the Lifecell® Adapter set. The other spike of the Plasma Transfer Set is inserted into the lead tube of the Lifecell® Adapter Set, assuring that all clamps are closed. A 2000 ml Transfer Pack Container (Fenwal® #4R2041) is hung on the final container hook of the Solution Transfer Pump and a final container connector is inserted into the Transfer Set junction.

In order to remove excess media from the ten-liter Aim V Flask, the Solution Transfer Pump is programmed following manufacturer's instructions to withdraw a volume of media equal to the volume of supplements to be added with the specific gravity set to 1.00. At the completion of the pumping cycle, the tubing leads from the Transfer Pack Container and media Flask are heat sealed. Lymphocyte activation media is prepared as in Example 1, substituting a 2000 ml Transfer Pack Container for the 300 ml container.

Cells are dispersed at a final concentration of about $5\times10^5$ cells/ml in Lymphocyte Activation Media according to the following ranges. For samples having less than about $5\times10^9$ white blood cells; about $5\times10^5$ white blood cells/ml are dispensed with Lymphoid Activation Media to a total volume of about 1L to about 1.5L per 3L Lifecell® Flask. For samples with greater than about $5\times10^9$ cells, about $7\times10^5$ white blood cells/ml are dispensed with about 1L to about 1.5L total volume per 3L Lifecell® Flask. The preferred total volume in a 3L Lifecell® Flask is about 1L, with a maximum volume of about 1.5L. Lifecell® Flasks are incubated on wire racks at about 37° C. at about 5% $CO_2$ for about 3 days.

Retroviral Transduction of T Lymphocytes

Activated T-cells are harvested using the double-chamber method of the Fenwal® CF3000 Plus (Baxter Fenwal® #4R4538). The double-chamber method uses the following material in addition to that used for the single-chamber method: 600 ml Transfer Pack Unit with coupler (Fenwal® #4R2023); a Lifecell® Flask (1000 ml capacity; Fenwal® #4R2110); and a Plasma Transfer Set with two couplers (Fenwal® #4C2243). An A35 chamber, instead of a small volume collection chamber, is inserted into the collection holder of the CS-3000® Plus. The priming procedure is as described above in Example 1.

The following steps are substituted in harvest procedure of Example 1 after the first two steps have been carried out. Two Plasma Transfer Sets are connected to a 600 ml Transfer Pack Container with coupler (the 600 ml Transfer Pack Container will be used as a "pooling pack"). The Transfer Pack Container is connected to the lead tube of the manifold(s). The Sterile Tubing Welder is used to attach a "Y" tubing lead obtained from an 800 ml Transfer Pack Unit (Fenwal® #4R2055) to one of the Plasma Transfer Sets. The "Y" tubing is spliced into line 5 (component rich plasma line) of the open system Apheresis Set. The other Plasma Transfer Set is attached to the inlet line. The roller clamps are then opened on both Plasma Transfer Sets. The saline and inlet clamps also are opened.

The inlet line to the Pooling Pack is primed by squeezing the prime media to push approximately 50 ml media to the pooling pack. The inlet clamp is then closed. A hemostat is placed above the junction on the component-rich plasma line. A blood pump (approx. 20 ml/min) is turned on to prime the line to the Pooling Pack. The Pooling Pack is filled with an additional 50 ml of media. The blood pump is turned off and the hemostat placed below the junction. The saline clamp is closed, and the vent and plasma return clamps are opened. The centrifuge is started, and when it reaches full speed (approximately 1600 rpm), the vent and plasma return clamps are closed.

The plasma collect clamp is then opened, ensuring that the Waste Flask is not occluded. Also, it is important to ensure that the roller clamps on the Plasma Transfer Sets leading to the pooling pack are open. The plasma flow direction switch is set to forward, and the plasma flow rate control is turned to 10 ml/min, ensuring that there is flow to the Waste Flask. The inlet and plasma return clamps are opened, and the blood flow rate control set to 10 ml/min, ensuring that there is flow to the Waste Flask. All roller clamps are opened to the culture Flasks and the pooling pack is allowed to fill. It is important to note that the roller clamp on the wash media is kept closed. Also, it may be necessary to place the Pooling Pack at a level below the culture Flasks. The flow rates of both pumps are increased to full speed (approx. 87 ml/min). When all culture Flasks have been emptied and the Pooling Pack is almost empty, all pumps are stopped, all clamps and closed and the centrifuge is stopped. The centrifuge compartment and the hemostat lines leading to each chamber are then opened. The resultant pellets are resuspended by gently massaging the appended Lifecell® Flasks. The Lifecell® Flasks are re-inserted into their respective chambers and the centrifuge door is closed. The roller clamp between the manifold set and the pooling pack is closed. The media is washed and allowed to fill the Lifecell® Flasks by opening the roller clamps, and the flasks rinsed by inversion. The roller clamp is opened to the pooling pack.

The above procedure is repeated to restart the centrifuge and the cells are washed by continuing to pump media. Once the media is emptied from the Pooling Pack, all of the pumps, the clamps and the centrifuge are turned off. The Lifecell® Flasks in both chambers are sealed off and enough of a lead on each Flask is retained to make a sterile connection. The Lifecell® Flasks in the CS-3000® are sterilely connected in order to pool both products into a Collection Flask. The Collection Flask is weighed to determine volume using an empty Flask to zero the scale.

The remainder of the procedure is substantially similar to that of Example 1, except that the three-liter Lifecell® Flasks are substituted for one-liter Lifecell® Flasks. In addition, the Lymphocyte Transduction Media was prepared from a ten-liter AIM V media Flask using a Fenwal® Solution Transfer Pump. The steps for the initial parameters for this Solution Transfer Pump are discussed above for the Lymphocyte Activation Media. The Lifecell® Flasks are then incubated overnight (rather than at least twelve hours).

Cell Maintenance and Expansion

About twenty-four hours after the addition of the retrovirus supernatant, the transduced white blood cells are harvested using the double-chamber method of the CS-3000® Plus. The rest of the procedure is substantially the same as Example 1, except that three-liter Lifecell® Flasks are substituted for the one-liter variety. For samples which have less than about $20 \times 10^9$ white blood cells, about $5 \times 10^5$ white blood cells/ml with about 1L to about 1.5L of Lymphocyte Culture Media are dispensed to each 3L Lifecell® Flask. For samples with greater than about $20 \times 10^9$ white blood cells, about $7 \times 10^5$ white blood cells/ml with about 1L to about 1.5L of Lymphocyte Culture Media are dispensed to each 3L Lifecell® Flask. The preferred media volume for each three-liter Lifecell® Flask is about 1L, with the maximum media volume being about 1.5L.

Lymphocyte Culture Media is prepared using a Fenwal® Solution Transfer Pump, in a manner similar to that used to prepare the Lymphocyte Activation Media and Retroviral Supernatant/Transduction Media (e.g., a ten-liter AIM V media Flask is manipulated using, in addition to the regular procedure, a Lifecell® Transfer Set, a Lifecell® Filter Adapater Set and a 2000 ml Transfer Pack Container).

The cell growth is aseptically monitored as described in Example 1. When cell densities reach approximately $2 \times 10^5$ cells/ml, the cells are split and reseed at about $5 \times 10^5$ cells/ml in additional Lymphocyte Culture Media. The white blood cells should be greater than about 90% viable, and the white blood cell concentration should be greater than about $5 \times 10^5$ cells/ml. The glucose concentration in the media should be greater than about 100 mg/dL, and the lactate concentration should be less than about 1.0 mg/ml. If the cells and media do not meet these criteria, then they are not suitable for later procedures.

G418 Selection of Neo-Transduced T Lymphocytes

After the cells are isolated using the double-chamber method on the CS-3000® Plus as described above, transduced white blood cells were resuspended in G418 selection media (made using the Fenwal® Solution Transfer Pump and a ten-liter Flask of AIM V). The selection media and cells are transferred into three-liter Lifecell® Flask using the Solution Transfer Pump according to the manufacturer's instructions. For samples with less than about $20 \times 10^9$ white blood cells, about $5 \times 10^5$ white blood cells/ml are dispensed with about 1L of G418 selection media to yield about 1.5L total media volume per Lifecell® Flask. For samples of transduced cells with greater than about $20 \times 10^9$ white blood cells in each Lifecell® Flask, about $7 \times 10^5$ white blood cells/ml are dispensed and enough G418 Selection Media added to yield a final volume of about 1L to about 1.5L total volume per Lifecell® Flask. The preferred media volume is about 1L per 3L Lifecell® Flask with the maximum volume of media being up to about 1.5L.

Cells can be fed with fresh G418 Selection Media after about three days. Transduced white blood cells can be harvested using the double chamber method on the CS-3000® as set forth above, or by other acceptable methods. With some donor cells, it may be necessary to split, dilute and reseed at the cells at about $5 \times 10^5$ white blood cells/ml if the cell density exceeds about $2 \times 10^6$ white blood cells/ml during G418 selection.

About five days after initiation of the selection, selected cells are harvested by washing gently in fresh Lymphocyte Culture Media. Transduced white blood cells can be harvested using the double chamber method using the CS-3000® Plus as discussed above or by other acceptable methods.

The transduced, G418-selected white blood cells are resuspended at about 1×10⁶ cells/ml in Lymphocyte Culture Media. The G418-selected white blood cells are monitored and cultured as above with the following variation. The viable cell density is maintained at about 1×10⁶ white blood cells/ml with frequent media exchanges until the resistant cells have undergone several rounds of cell division, at which time seeding density may be reduced to about 5×10⁵ white blood cells/ml.

Cryopreservation and Subsequent Thawing of Cells

This procedure is carried out substantially as in Example 1, except the Fenwal® Cell Harvester (Baxter Fenwal® #4R4960) is used to harvest the transduced, G418-selected cells. The Fenwal® Cell Harvester is used in conjunction with a Fenwal® Mobile Work Station (Baxter Fenwal® #4R4962). Components that were used with the Fenwal® Plasma Extractor in Example 1 are also applicable to this Example. The Fenwal® Cell Harvester is used as set forth in the operator's manual.

Cell Monitoring and Sampling Procedures

Generally, at a minimum, culture and cell monitoring is performed on the initial product, and at the initiation and completion of each processing step. The choice of assays will depend on the equipment and resources available. Specific methods of monitoring are set forth in Example 1.

EXAMPLE 3

Preparation of Retroviral Vector Backbones

This example describes the construction of several retroviral backbones useful in the preparation of the gene transfer vectors of the present invention.

A. Preparation of pKT-1 and pKT-3B vectors.

The Moloney murine leukemia virus (MOMLV) 5' long terminal repeat (LTR) EcoRI-EcoRI fragment (including gag sequences) from the N2 vector (Armentano et al. (1987) *J. Virol.* 61:1647–1650, Eglitas et al. (1985) *Science* 230:1395–1398) is ligated into the plasmid SK+ (Stratagene, La Jolla, Calif.). The resulting construct is designated N2R5. The N2R5 construct is mutated by site-directed in vitro mutagenesis to change the ATG start codon to ATT preventing gag expression. This mutagenized fragment is 200 base pairs (bp) in length and flanked by PstI restriction sites. The PstI-PstI mutated fragment is purified from the SK+ plasmid and inserted into the PstI site of N2 MoMLV 5' LTR in plasmid pUC31 to replace the non-mutated 200 bp fragment. The plasmid pUC31 is derived from pUC19 (Stratagene, La Jolla, Calif.) in which additional restriction sites XhoI, BglII, BssHII and NcoI are inserted between the EcoRI and SacI sites of the polylinker. This construct is designated pUC31/N2R5gM.

A 1.0 kilobase (Kb) MOMLV 3' LTR EcoRI-EcoRI fragment from N2 is cloned into plasmid SK+ resulting in a construct designated N2R3-. A 1.0 Kb ClaI-HindIII fragment is purified from this construct.

The ClaI-ClaI dominant selectable marker gene fragment from the pAFVXM retroviral vector (Kriegler et al. (1984) *Cell* 38:483, St. Louis et al. (1988) *Proc. Natl. Acad. Sci. U.S.A.* 85:3150–3154), comprising a SV40 early promoter driving expression of the neomycin (neo) phosphotransferase gene, is cloned into the SK+ plasmid. This construct is designated SK+SV2-neo. A 1.3 Kb ClaI-BstBI gene fragment is purified from the SK+ SV2-neo plasmid.

KT-3B or KT-1 vectors are constructed by a three part ligation in which the XhoI-ClaI fragment containing a gene of interest, and the 1.0 Kb MOMLV 3' LTR ClaI-HindIII fragment are inserted into the XhoI-HindIII site of pUC31/N2R5gM plasmid. This gives a vector designated as having the KT-1 backbone. The 1.3 Kb ClaI-BstBI neo gene fragment from the PAFVXM retroviral vector is then inserted into the ClaI site of this plasmid in the sense orientation to yield a vector designated as having the KT-3B backbone.

B. Preparation of DBA-5a, pBA-5b, pBA-5c, pBA-9b and pBA-8bL1.

Several modifications can be made to the retroviral vector pKT-1 which result in decreased sequence homology to the retroviral gag/pol and envelope expression constructs. In addition, two stop codons were introduced in the DNA sequence of the packaging signal sequence in order to increase the safety of these vectors. The resulting retroviral backbones are called pBA-5a, pBA-5b, and pBA-5c. Further details on the construction of pBA-5a, pBA-5b and pBA-5c can be found in co-owned U.S. patent application Ser. No. 08/721,327 now abandoned and co-owned U.S. patent application entitled "Crossless Retroviral Vectors," filed May 5, 1997 (attorney docket 1147.004) both of which are hereby incorporated by reference.

Substitution of Nonsense Codons in the Extended Packaging Sequence (ψ+)

Modification of the extended packaging signal (ψ+) was conducted using PCR on the template KT-1 with primers that introduce two stop codons in the extended packaging signal sequence. In particular, the template pKT-1 contains the modification ATT at the normal ATG start site of gag. Here the start site was further modified to the stop codon, TAA, and an additional stop codon TGA was added to replace the codon TTA at position 645–647 of the sequence depicted in SEQUENCE ID NO: 15 of co-owned U.S. provisional application entitled "Methods for Administration of Recombinant Gene Delivery Vehicles for Treatment of Hemophilia and Other Disorders," filed Jun. 4, 1997 (attorney docket 1155.004), which application is incorporated herein by reference.

Briefly, two sets of PCR reactions were carried out on pKT-1, each introducing one stop codon. The primers for the PCR were designed such that the two PCR products had overlapping regions and a splice-overlap extension PCR (SOE-PCR) was carried out with the two PCR products in order to combine the two introduced stop codons on one strand. The first set of oligonucleotides introducing the change from ATT to TAA were:

5'-GGG AGT GGT AAC AGT CTG GCC TTA ATT CTC AG SEQ ID NO:1; and

5'-CGG TCG ACC TCG AGA ATT AAT TC SEQ ID NO:2, and the second set of oligonucleotides introducing the change from TTA to TGA were:

5'-CTG GGA GAC GTC CCA GGG ACT TC SEQ ID NO:3; and

5'-GGC CAG ACT GTT ACC ACT CCC TGA AGT TTG AC SEQ ID NO:4.

The flanking primers of the final 708 base pair PCR product introduced AatII and the XhoI sites, at the 5' and 3' ends, respectively.

The ends of the 708 base pair product were blunted and phosphorylated, and the product introduced into the SmaI and EcoRV digested vector pBluescript SK– (Stratagene, San Diego, Calif.). The resulting plasmid was designated pBA-2.

Removal of Retroviral Sequences Upstream and Downstream from the 3' LTR and Upstream and within the 5' LTR Retroviral envelope sequence was removed upstream of the 3' LTR between the ClaI site and the TAG stop codon of the envelope coding sequence. The DNA sequence was modified by PCR such that the TAG stop codon was replaced by a ClaI site and the 97 nucleotides upstream from this new ClaI site to the original ClaI site were deleted, as well as the 212 base pairs of retroviral sequence downstream of the 3' LTR.

Briefly, the following two oligonucleotides were used for the PCR:

5'-CAT CGA TAA AAT AAA AGA TTT TAT TTA GTC SEQ ID NO:5; and

5'-CAA ATG AAA GAC CCC CGC TGA C SEQ ID NO:6, and the template was pKT-1. The PCR product was cloned into PPCRII (Invitrogen, San Diego, Calif.) using the TA cloning kit (Invitrogen, San Diego, Calif.) and called pBA-1.

Subsequently, pBA-2 was digested with XbaI and AatII which deleted a part of the multiple cloning site and the 780 base pair fragment from NheI to AatII from pKT1 was cloned into the linearized vector, resulting in the plasmid pBA-3. Plasmid pBA-3 combined the shortened 5' LTR with the above-described packaging region including the two introduced stop codons.

The pBA-1 construct was then digested with ClaI and ApaI to obtain a 640 base pair fragment that was cloned into the ClaI and ApaI-digested pBA-3, resulting in the plasmid pBA-4. This plasmid combines the above-described 5' LTR and the packaging signal with the 3' LTR.

pBA-4 was digested with ApaI and EcoRI, blunt-end modified, and religated in order to remove extraneous 3' polylinker sites, resulting in plasmid pBA-5a.

Subsequently, pBA-5a was cut with NotI (blunted) and EcoRI, and introduced into SmaI and EcoRI-digested pUC18 (GIBCO/BRL, Gaithersburg, Md.) resulting in pBA-5b. This construct moved the retroviral vector from a pBluescript backbone into an alternate pUC18 vector.

pBA-5c is constructed in identical manner to pBA-5b, except that the XhoI/ClaI multicloning site was introduced into pUC-19.

Several further modifications to the retroviral vector pBA-5b were carried out to provide a vector with multiple unique restriction enzyme sites for convenient cloning. In order to prepare the pBA-9b vector, the herpes simplex virus thymidine kinase (HSVTK) gene was retrieved by digesting the pBH-1 construct with XhoI and EcoRI, resulting in a 1.2 Kb fragment. (pBH-1 was prepared as described in International Publication No. WO 91/02805, entitled "Recombinant Retroviruses Delivering Vector Constructs to Target Cells," which is hereby incorporated by reference.) The neomycin gene driven by the SV40 promoter was retrieved by digesting pKT-1 with EcoRI and BstBI, resulting in a 1.3 Kb fragment. Both fragments were cloned into a XhoI and Cla-digested pBA-5b, resulting in the retroviral vector pMO-TK.

The TK gene from the retroviral vector pMO-TK was isolated as a XhoI-ClaI fragment and inserted into the XhoI and ClaI-digested pBA-5b, resulting in the plasmid pBA-5bTK. In order to delete the HindIII, SphI, PstI, SalI and HincII restriction enzyme sites upstream of the 5' LTR, pBA-5bTK was digested with HindIII and HincII, and the overhanging ends were removed using T4 polymerase and the blunt ends ligated using T4 DNA ligase. This resulted in plasmid pTJBA-5bTK with 16 bases (TGC ATG CCT GCA GGT C) (SEQ ID NO2) removed from the region upstream of the 5' LTR. The plasmid pTJBA-5bTK has a BamHI upstream of the 5' LTR. It is desirable to remove this BamHI site since it is a common site used for cloning. In order to destroy the BamHI site upstream of the 5' LTR, the BamHI-containing TK gene in pTJBA-5bTK was replaced by the IL-2 gene via a XhoI and ClaI digest, resulting in plasmid pTJBA-5bIL-2. The plasmid pTJBA-5bIL-2 was digested with BamHI, the ends filled in with the Klenow fragment and religated, resulting in pTJBA-5bIL-2 (BamHI del.).

In order to produce the plasmid pBA-9b, the IL-2 gene from pTJBA-5bIL-2 (BamHI del.) is deleted via XhoI-ClaI digest, and replaced with a polylinker that introduces a multiple cloning site (MCS) and codes for the restriction enzyme sites 5'-XhoI ApaI BglII NotI NruI SalI HindIII BamHI ClaI-3'. The sequences of the two primers used to produce the linker are as follows:

5'-TCG AGG GGC CCA GAT CTG CGG CCG CTC GCG AGT CGA CAA GCT TGG ATC CAT-3' SEQ ID NO:7 (as the primer for the positive strand); and 5'-CGA TGG ATC CAA GCT TGT CGA CTC GCG AGC GGC CGC AGA TCT GGG CCC C-3' SEQ ID NO:8 (as the primer for the negative strand).

This example also describes several modifications of the retroviral vector pBA-5b which result in a vector coding for the human placental alkaline phosphatase gene (PLAP), driven by the SV40 promoter.

The plasmid pBA-8bL1 was constructed in a three-way ligation using the following three fragments: (1) the NdeI-ClaI fragment from pBA-5b (described above) containing the 3' LTR and the pUC18 backbone; (2) the ClaI-HindIII fragment from pCI-PLAP coding for PLAP; and (3) the HindIII-NdeI fragment from pBA-6bL1 containing the 5' LTR and the SV40 promoter. Plasmid pBA-6bL1 is based on pBA-6b (described above) wherein the HIV env/rev coding region was deleted via a XhoI-ClaI digest, and replaced with the L1 linker coding for several restriction enzyme sites including XhoI at the 5' end and ClaI at the 3' end.

EXAMPLE 4

Preparation of pBA-5a, pBA-5b, and pBA-5c
Retroviral Vectors Expressing B Domain-Deleted
Factor VIII A B domain-deleted factor VIII cDNA fragment was obtained by a XhoI/NotI digestion as described below. A retroviral vector (pMBF8) expressing a B domain-deleted factor VIII is constructed from the expression plasmid pSVF8-200 which is prepared as previously described (Truett (1985) *DNA* 4:333 and U.S. Pat. No. 5,045,455). The pSVF8-200 plasmid was deposited with the ATCC 10801 University Boulevard, Manassas, Va., on Jul. 17, 1985, and assigned ATCC Accession No. 40190.

A DNA fragment encoding the B domain-deleted Factor VIII molecule was obtained from pSVF8-302, which has a nine base pair deletion in the 5' non-coding region after the poly G tail. Plasmid SVF8-302 was constructed in a similar manner as pSVF8-200, which is described in detail in Truett, supra, and in U.S. Pat. No. 5,045,455. Construction of pSVF8-302 is also described in U.S. Pat. No. 5,595,886.

The procedure outlined below describes the construction of retroviral vectors expressing a B domain-deleted Factor VIII protein obtained from pSVF8-302. However, the same procedure can also be used to construct such retroviral vectors from pSVF8-200.

The full-length cDNA sequence of human factor VIII, and the full-length amino acid sequence thereof are disclosed in co-owned U.S. provisional application entitled "Methods for Administration of Recombinant Gene Delivery Vehicles for Treatment of Hemophilia and Other Disorders," filed Jun. 4, 1997 (attorney docket 1155.004). The cDNA sequence of the B domain-deleted SQN deletion, and the SQN deletion amino acid sequence are also disclosed in the above-reference provisional patent application.

Fragment 1, encompassing nucleotides 5500–6248 of pSVF8-200 (see FIG. 8 of Truett, supra), was obtained by VENT-PCR using factor VIII primers encoding a PflM1 site at the 3' end and the 5' SQN sequence plus a HindIII site at the 5' end. The 5' primer encompasses the region 2446–2460 of the 5' SQN and the 5144–5167 region just downstream of the 3' SQN sequence. Thus, this fragment spans the sequence between the two SQN sites within the B domain (positions 2461 and 5142). The particular primer sequences used were:

```
5'-GAA GCT TCT CCC AGA ACC CAC CAG TCT TGA AAC
GCC ATC SEQ ID NO:9; and

5'-GTA CCA GCT TTT GGT CTC ATC AAA G SEQ ID
NO:10.
```

Fragment 1 was blunt-end cloned into vector SK– that had been cut with SmaI and dephosphorylated, forming pSK-Pfl. Fragment 2, encompassing nucleotides 1190–2448, was isolated following HindIII digestion and cloned into the HindIII site of SK-Pfl to form SK-Pfl-Hind. The orientation of the insert was determined using AccI and PstI digests. pSVF8-200 was digested with HpaI and religated to remove two small HpaI fragments 3' to the factor VIII cDNA insert, forming pF8-300-del-Hpa. The remaining HpaI site was converted to a NotI site using NotI phosphorylated linkers, forming F8-300-Hpa/Not.

Fragment 3, encompassing nucleotides 5885–7604, was isolated after a PflM1 and NotI digestion, and cloned into SK-Pfl-Hind following PflM1 and NotI digestion of the latter to form pF8:213. Fragment 4 (encompassing nucleotides 104–133 to 1204) was obtained following VENT-PCR of PSV7dF8-300 with primers containing 5' XhoI and 3' AccI sites respectively. The 5' primer encompasses nucleotides 104–133, and the 3' primer encompasses nucleotides 1200–1224. pF8:213 was digested sequentially with XhoI followed by AccI, and ligated to Fragment 4 which was digested with XhoI and AccI, to provide pF8:4213. The primer sequences for the 5' UT and XhoI primers were:

```
5'-CTC CTC GAG CTA AAG ATA TTT TAG AGA AGA ATT
AAC SEQ ID NO:11; and

5'-TTC CTC TGG ACA GCT GTC TAC TTT G SEQ ID
NO:12.
```

The above-described modified cDNA is cloned into the pMBA backbone (also described above) which has been digested with XhoI and NotI. Similarly, the crossless backbones pBA-9b, pBA-5a, pBA-5b and pBA-5c are modified by linearizing with ClaI, blunt-end modifying, and religating in the presence of NotI phosphorylated linkers. The modified cDNA fragment is cloned into the XhoI/NotI linearized vectors.

EXAMPLE 5

Construction of Recombinant Adeno-Associated Virus (rAAV) Vectors that Express the Heavy and Light Chains of Human Factor VIII This example describes the construction of two rAAV gene transfer vectors, one expressing the light chain, and the other the heavy chain of human factor VIII. Both chains contain the Factor VIII leader sequence and a variable amount of the B domain.

To clone the heavy chain, a region of the Factor VIII gene, from 174 bp 5' of the ATG, to amino acid 745, was amplified by PCR. This fragment includes the entire heavy chain and the first five amino acids of the B domain. The oligos used were:

```
(forward) 5'-CAC CGT CGT CGA CTT ATG CT-3' SEQ ID NO:13; and (reverse) 5'-GAC CGT CGA CTC AAT TCT GGG AGA
AGC TTC TTG G-3' SEQ ID NO:14.
```

AGC TTC TTG G-3' SEQ ID NO:14. The plasmid used as a template in the PCR reaction was pCMVKmHSTB, a B domain-deleted factor VIII expression construct. The amplified fragment was digested with SalI, and cloned into a CMV expression vector, pCMVKmLINK digested with SalI and XhoI. This plasmid was called pCMVKm9OH. pCMVkM-LINK is an expression vector containing the CMV promoter/intron, a polylinker for cloning genes of interest, and a bovine growth hormone polyadenylation signal. To make a rAAV vector expressing the heavy chain, pCMVKm9OH was digested with SalI and BamHI, the BamHI site was filled in with T4 DNA polymerase, and this fragment was cloned into the rAAV vector pKm201CMV-CI digested with SalI and EcoRV. pKm201CMV-CI contains the inverted terminal repeats of AAV, the CMV promoter, the chimeric intron from pCI (Promega, Madison, Wis.), and the bovine growth hormone polyadenylation signal. The final AAV vector was called pKm201-90H.

To clone the light chain, the factor VIII 5' untranslated and leader region sequences were amplified using the following primers:

```
    (forward) 5'-CAC CGT CGT CGA CTT ATG CT-3' SEQ ID NO:15; and (reverse) 5'-CAA CGC TCG AGA AGC AGA ATC GCA
AAA GGC-3' SEQ ID NO:16.
```

Again, pCMVKmHSTB was used as a template in the PCR reaction. The amplified region includes sequences from 174 bp upstream of the ATG, to amino acid 19 of factor VIII. This fragment was digested with XhoI and SalI and cloned into pCMVKmLINK digested with XhoI and SalI. This plasmid was called pCMVKmF8L (for factor VIII leader). To amplify the light chain, the following primers were used:

```
     (forward) 5'-TCG GCT CGA GGC ATC AAC GGG AAA
TAA CTC GT-3' SEQ ID NO:17; and (reverse) 5'-CCG ACT CGA GTC AGT AGA GGT CCT
GTG CCT C-3' SEQ ID NO:18.
```

Again, pCMVkMHSTB served as the template for the PCR. The amplified fragment included sequences from amino acid 1645 of factor VIII to the STOP codon after amino acid 2332. This included the last four amino acids of the B domain and the complete light chain. This fragment was digested with XhoI and cloned into the XhoI site of pCMVKmF8L. This resulted in a light chain construct containing the factor VIII leader which was called pCMVKm80L. pCMVKm80L was digested with SalI and BamHI to remove the light chain construct, and this fragment was cloned into pKm201CMV-CI digested with SalI and BamHI to generate pKm201-80L.

EXAMPLE 6

Co-Infection of Cells with rAAV Vectors Expressing the Heavy and Light Chains of Factor VIII Results in the Production of Biologically Active Factor VIII The heavy and light chain constructs, pKm201-80L and pKm201-90H, were packaged following standard procedures for the production of rAAV (Zhou et al. (1994) *J. Exp. Med.* 179:1867–1875). rAAV was purified as described (Wang et al. (1995) *Proc. Natl. Acad. Sci. U.S.A.* 92:12416–12420) and used to infect 293 cells plated in 6-well plates. Supernatants of infected cells were collected 48 h after infection and assayed for biologically active factor VIII by Coamatic Factor VIII (KabiVitrum, Stockholm), following the manufacturer's instructions. Normal human plasma (George King Bio-Medical, Inc., Overland Park, Kans.) was used to generate a standard curve. Cells were infected at a multiplicity of infection (MOI) of 6000 rAAV particles per cell. The experiment was done both with and without the addition of etoposide (0.3 M) to the medium. Etopiside has been shown to increase the transduction efficiency of rAAV vectors (Russell et al. (1995) *Proc. Natl. Acad. Sci. U.S.A.* 92:51719–51723). As a result of the study, co-infection of rAAV-80L and rAAV-90H resulted in the production of biologically active factor VIII. The amount of factor VIII was increased in the presence of etoposide.

EXAMPLE 7

Construction of a Retroviral Vector Expressing Human LDL Receptor

This experiment describes the production of a retroviral gene transfer vector expressing human LDL-receptor. The human LDL-receptor expression plasmid pLDLR17 was obtained from Bev Davidson, at the University of Iowa. Alternatively, the expression plasmid can be prepared as described by (1989) *J. Biol. Chem.* 264:21682–88. The 5' fragment was reconstructed using VENT-PCR. The 3' primer contained a XhoI site, and the 3' primer encompasses the unique EcoRI site within the LDLR cDNA. The EcoRI-digested 5' fragment was subcloned into Bluescript SK– and cut with SmaI and EcoRI. The SmaI site at the 3' end of LDLR cDNA in LDLR17 was modified using a NotI linker to yield pLDLR17-S/N. The two fragments (the 5' fragment: XhoI to EcoRI, and the 3' fragment: EcoRI to NotI) were ligated to pBA-6b which was digested with XhoI and NotI. The sequences of the PCR primers were:

```
5'-GCG ACT CGA GCA TGG GGC CCT GGG GC SEQ ID NO:19;

and

5'-GCA CTG GAA TTC GTC AGG GCG SEQ ID NO:20.
```

The resulting vector was named p6b-LDLR.

A high titer DA producer clone for p6b-LDLR was selected under G418. The G418 vector titer in the supernatant was around $2 \times 10^7$ cfu/ml. Expression in target cells in vitro was demonstrated to be comparable to normal levels using either a Western blot or a functional assay.

EXAMPLE 8

Human Alpha 1 Antitrypsin Retroviral Vectors for the Treatment of Antitrypsin Deficiency This example describes the preparation of a retroviral gene transfer vector encoding human $\alpha_1$-antitrypsin. The human $\alpha_1$-antitrypsin cDNA clone was obtained from the ATCC (Clone #256976). The plasmid was digested with EcoRI and blunted using T4 DNA polymerase large fragment (Klenow). The fragment containing the cDNA is cloned into the SrfI linearized pBA-9 vector to produce the provector pBA9-AAT. An oxidation resistant cDNA clone prepared as described in U.S. Pat. No. 4,732,973 was digested with restriction enzymes and ligated to pBA-5b.

Accordingly, methods for genetically modifying a population of T cells, and gene transfer vectors for carrying out the modifications are disclosed. Although preferred embodiments of the subject invention have been described in some detail, it is understood that obvious variations can be made without departing from the spirit and the scope of the invention as defined by the appended claims.

We claim:

1. A method for producing a population of transduced T cells, said method comprising:
   (a) providing an in vitro population of T cells;
   (b) activating the T cells by contacting said population with a CD3 binding agent; and
   (c) transducing activated T cells obtained in step (b) by contacting said activated T cells with a gene transfer vector, wherein transduction is carried out when the cell density of the activated T cell population is between about $0.1 \times 10^6$ and $5 \times 10^6$.

2. The method of claim 1, wherein transduction in step (c) is carried out when the cell density of the activated T cell population is between about $0.5 \times 10^6$ and $2 \times 10^6$.

3. The method of claim 1, wherein the gene transfer vector comprises a promoter operably linked to a first nucleotide sequence which, when expressed, provides a transduced cell with enhanced susceptibility to a selected cytotoxic agent.

4. The method of claim 3, wherein the gene transfer vector further comprises a second nucleotide sequence encoding a selectable marker.

5. The method of claim 1, further comprising a selection step which comprises fluorescence-activated cell sorting (FACS) of the T cells obtained after step (c), whereby non-transduced T cells can be separated from transduced T cells.

6. The method of claim 1, wherein the gene transfer vector is a retroviral vector.

7. The method of claim 1, wherein the T cell population is contacted with the CD3 binding agent in step (b) for 3 to 4 days.

8. The method of claim 1, wherein the CD3 binding agent is an antibody molecule specific for CD3.

9. The method of claim 1, wherein transduction in step (c) is carried out with a viral vector at a multiplicity of infection (MOI) of about 3 or greater.

10. The method of claim 3, wherein the first nucleotide sequence is a suicide gene.

11. The method of claim 10, wherein the first nucleotide sequence is a Herpes Simplex Virus thymidine kinase (HSV-tk) gene.

12. The method of claim 11, wherein the gene transfer vector further comprises a selectable marker.

13. The method of claim 11, wherein the gene transfer vector is a retroviral vector.

14. The method of claim 4, wherein the selectable marker provides a transduced T cell with resistance to a selected cytotoxic agent.

15. The method of claim 4, wherein the selectable marker is a cell surface marker.

16. The method of claim 14, wherein the selectable marker is neomycin phosphotransferase II.

17. The method of claim 14, further comprising a selection step which comprises: contacting the T cells obtained after step (c) with the selected cytotoxic agent, whereby non-transduced T cells can be negatively selected away from the population.

18. The method of claim 15, further comprising a selection step which comprises: contacting the T cells obtained after step (c) with a binding molecule specific for the cell surface marker, whereby transduced T cells can be positively selected away from the population.

19. The method of claim 11, wherein the selectable marker is neomycin phosphotransferase II.

20. The method of claim 18, wherein the selection step comprises fluorescence-activated cell sorting (FACS) of the T cells obtained after step (c).

21. The method of claim 8, wherein the antibody molecule is an OKT-3 antibody.

22. A method for producing a population of transduced T cells, said method comprising:

(a) providing an in vitro population of T cells;

(b) activating the T cells by contacting said population with a CD3 binding agent and a mitogen; and (c) transducing activated T cells obtained in step (b) by contacting said activated T cells with a gene transfer vector, wherein transduction is carried out when the cell density of the activated T cell population is between about $0.1 \times 10^6$ and $5 \times 10^6$.

23. The method of claim 22, wherein the mitogen in step (b) is a cytokine.

24. The method of claim 22, wherein transduction in step (c) is carried out when the cell density of the activated T cell population is between about $0.5 \times 10^6$ and $2 \times 10^6$.

25. The method of claim 22, wherein the gene transfer vector comprises a first nucleotide sequence which, when expressed, provides a transduced cell with enhanced susceptibility to a selected cytotoxic agent.

26. The method of claim 22, wherein the gene transfer vector is a retroviral vector.

27. The method of claim 23, wherein the cytokine is IL-2.

28. The method of claim 27, wherein the IL-2 contacted with the population of T cells in step (b) is added to the population at a concentration of about 50 to 100 µg/mL.

29. The method of claim 25 wherein the first nucleotide sequence is a suicide gene.

30. The method of claim 29, wherein the first nucleotide sequence is a Herpes Simplex Virus thymidine kinase (HSV-tk) gene.

31. The method of claim 30, wherein the retroviral vector is added to the activated T cell population in step (c) at a multiplicity of infection (MOI) of about 3 or greater.

32. A method for producing a population of transduced T cells, said method comprising:

(a) providing an in vitro population of T cells;

(b) activating the T cells by contacting said population with a CD3 binding agent;

(c) washing the activated T cell population obtained in step (b) and re-seeding the activated T cells at a cell density of about $5 \times 10^5$; and (d) transducing the activated T cell population obtained in step (c) by contacting said activated T cells with a gene transfer vector, wherein transduction is carried out when the cell density of the activated T cell population is between about $5 \times 10^5$ and $2 \times 10^6$.

33. The method of claim 32, wherein the gene transfer vector comprises a first nucleotide sequence which, when expressed, provides a transduced cell with enhanced susceptibility to a selected cytotoxic agent.

34. The method of claim 32, wherein the gene transfer vector is a retroviral vector.

35. The method of claim 33 wherein the first nucleotide sequence is a suicide gene.

36. The method of claim 35, wherein the first nucleotide sequence is a Herpes Simplex Virus thymidine kinase (HSV-tk) gene.

37. A method for producing a nonselected population of transduced T cells, said method comprising:

(a) providing an in vitro population of T cells;

(b) activating the T cells by contacting said population with a CD3 binding agent;

(c) transducing activated T cells obtained in step (b) by contacting said activated T cells with a retroviral vector at a multiplicity of infection (MOI) of about 3 or greater, wherein transduction is carried out when the cell density of the activated T cell population is between about $5 \times 10^5$ and $2 \times 10^6$.

38. The method of claim 37, wherein the retroviral vector comprises a first nucleotide sequence which, when expressed, provides a transduced cell with enhanced susceptibility to a selected cytotoxic agent.

39. The method of claim 38 wherein the first nucleotide sequence is a suicide gene.

40. The method of claim 39, wherein the first nucleotide sequence is a Herpes Simplex Virus thymidine kinase (HSV-tk) gene.

41. A kit for producing a population of transduced T cells, said kit comprising a CD3 binding agent contained in one or more containers, a gene transfer vector contained in one or more containers, magnetic particles and cell selecting reagents, optional hardware, and instructions for use of the kit.

42. The kit of claim 41, wherein the CD3 binding agent is an antibody molecule specific for CD3.

43. The kit of claim 41, wherein the gene transfer vector comprises a promoter operably linked to a first nucleotide sequence which, when expressed, provides a transduced cell with enhanced susceptibility to a selected cytotoxic agent.

44. The kit of claim 41, wherein the gene transfer vector further comprises a second nucleotide sequence encoding a selectable marker.

45. The kit of claim 42, wherein the antibody molecule is an OKT-3 antibody.

46. The kit of claim 43 wherein the first nucleotide sequence is a suicide gene.

47. The kit of claim 46, wherein the first nucleotide sequence is a Herpes Simplex Virus thymidine kinase (HSV-tk) gene.

48. The kit of claim 44, wherein the selectable marker is capable of providing a transduced T cell with resistance to a selected cytotoxic agent.

49. The kit of claim 48, wherein the selectable marker is neomycin phosphotransferase II.

50. The kit of claim 48, wherein the selectable marker is a cell surface marker.

* * * * *